United States Patent
Carew et al.

(10) Patent No.: US 11,293,913 B2
(45) Date of Patent: Apr. 5, 2022

(54) CONTAINER FOR RAPID BLOOD DETECTION AND BLOOD LOSS ASSESSMENT

(71) Applicant: Cypher Medical, LLC, Fair Oaks Ranch, TX (US)

(72) Inventors: Christopher A. Carew, Fair Oaks Ranch, TX (US); Jian Ling, Spring Branch, TX (US)

(73) Assignee: Cypher Medical, LLC, Boerne, TX (US)

( * ) Notice: Subject to any disclaimer, the term of this patent is extended or adjusted under 35 U.S.C. 154(b) by 0 days.

(21) Appl. No.: 16/257,876

(22) Filed: Jan. 25, 2019

(65) Prior Publication Data
US 2019/0154659 A1 May 23, 2019

Related U.S. Application Data

(62) Division of application No. 15/868,983, filed on Jan. 11, 2018, now Pat. No. 10,401,347.

(Continued)

(51) Int. Cl.
*G01N 33/49* (2006.01)
*G01N 1/40* (2006.01)
(Continued)

(52) U.S. Cl.
CPC .............. *G01N 33/491* (2013.01); *A61J 1/00* (2013.01); *G01N 1/4077* (2013.01); *G01N 9/02* (2013.01);
(Continued)

(58) Field of Classification Search
CPC ...... G01N 33/491; G01N 1/4077; G01N 9/02; G01N 15/05; A61J 1/00
See application file for complete search history.

(56) References Cited

U.S. PATENT DOCUMENTS 4,801,428 A  1/1989 Homolko et al.
5,945,004 A  8/1999 Ohira et al.
(Continued)

FOREIGN PATENT DOCUMENTS

AU   2019216661 A1   9/2019
EP     0819437 A1    1/1998
(Continued)

OTHER PUBLICATIONS

PCT International Search Report and Written Opinion, PCT Application No. PCT/US2018/013407, dated Jan. 11, 2017, 14 pages.

*Primary Examiner* — Brian R Gordon
*Assistant Examiner* — Dwan A Gerido
(74) *Attorney, Agent, or Firm* — Denise L. Mayfield; Dykema Gossett PLLC

(57) ABSTRACT

Disclosed are methods, materials and devices for approximation of blood volume in a fluid, such as in a biological fluid collected during a surgical procedure. The method and devices include the use of a RBC flocculant, such as polyDADMAC, and an approximate blood hematocrit for the type of animal, as well as a calculated RBC packing ratio corresponding to the collection device being used. Also provided is a Blood Indicator Panel (BIP), comprising a series of markings calculated from an observed red blood settlement volume, the average animal type hematocrit, and a calculated RBC packing ratio "η" value for the collection device. Pediatric (about 200 ml or 250 ml size container), adult human (about 1,000 ml-1,500 ml) and veterinary (about 500 ml-2,500 ml) collection containers are also disclosed, that include a RBC flocculant, for use in approximating blood volume in a fluid.

15 Claims, 30 Drawing Sheets

Related U.S. Application Data

(60) Provisional application No. 62/445,067, filed on Jan. 11, 2017.

(51) Int. Cl.
*G01N 15/05* (2006.01)
*G01N 9/02* (2006.01)
*A61J 1/00* (2006.01)

(52) U.S. Cl.
CPC ..... *G01N 15/05* (2013.01); *G01N 2001/4083* (2013.01); *G01N 2009/026* (2013.01)

(56) References Cited

U.S. PATENT DOCUMENTS

| | | | |
|---|---|---|---|
| 7,430,478 | B2 | 9/2008 | Fletcher-Haynes et al. |
| 7,499,581 | B2 | 3/2009 | Tribble et al. |
| 7,743,928 | B2 | 6/2010 | Crowley et al. |
| 7,981,019 | B2 | 7/2011 | Holmes et al. |
| 8,123,731 | B2 | 2/2012 | Ryan |
| 8,454,831 | B2 | 6/2013 | Sauvignet et al. |
| 8,792,693 | B2 | 7/2014 | Satish et al. |
| 9,365,814 | B2 | 6/2016 | Bachur, Jr. et al. |
| 9,652,655 | B2 | 5/2017 | Satish et al. |
| 2011/0147304 | A1* | 6/2011 | Sauvignet .......... C02F 1/52 210/608 |
| 2011/0178424 | A1 | 7/2011 | Wilkinson et al. |
| 2012/0309636 | A1 | 12/2012 | Gibbons et al. |
| 2013/0186834 | A1 | 7/2013 | Vicalvi et al. |
| 2013/0303870 | A1 | 11/2013 | Satish et al. |
| 2017/0290518 | A1* | 10/2017 | Akerman .......... G01N 33/49 |
| 2018/0028431 | A1* | 2/2018 | Chiattello .......... C08L 39/00 |

FOREIGN PATENT DOCUMENTS

| | | | |
|---|---|---|---|
| JP | H 095681 | * | 3/1997 |
| JP | H 0956810 | * | 3/1997 |
| JP | H0956810 | A | 3/1997 |
| WO | 2013172874 | A1 | 11/2013 |
| WO | 2018132619 | A1 | 7/2018 |

* cited by examiner

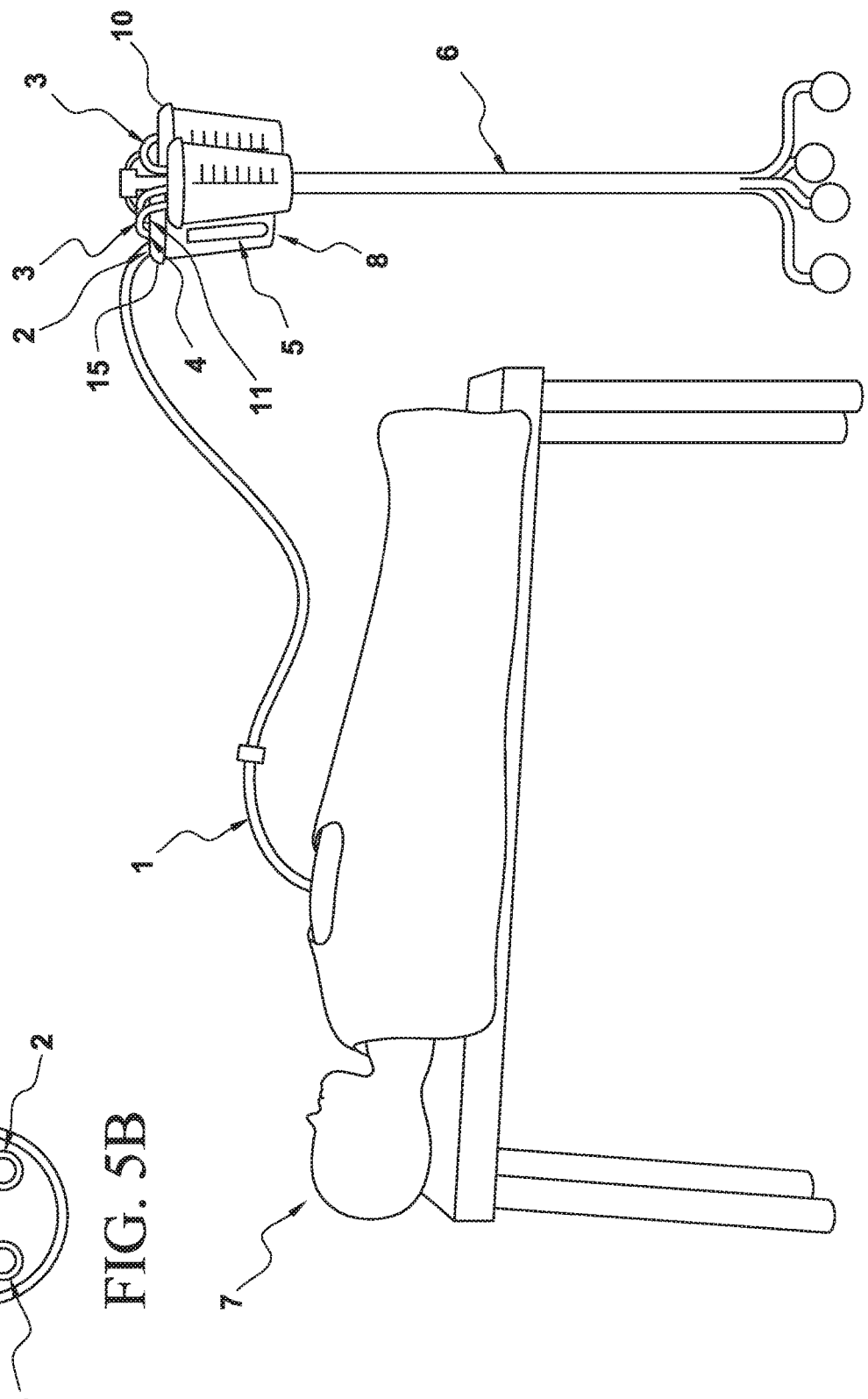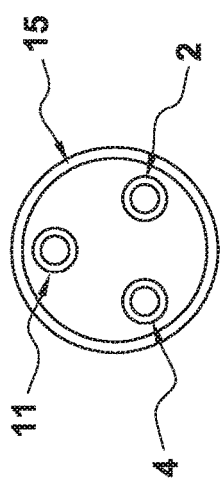

CONTAINER FOR RAPID BLOOD DETECTION AND BLOOD LOSS ASSESSMENT

RELATED APPLICATIONS

The present application claims priority to U.S. Provisional Patent Application 62/445,067, filed Jan. 11, 2017, and is a Divisional of U.S. patent application Ser. No. 15/868,983 filed on Jan. 11, 2018, currently pending. Both are incorporated herein in their entirety.

BACKGROUND OF THE INVENTION

During surgery, blood, saline, and in some cases, small tissue are evacuated from a subject's body, and collected in a collection container. Typically, this evacuation process is accompanied by suction. The components in the collection canister include at least some volume of blood in most cases. However, the volume of blood included is difficult to assess with any degree of accuracy. Blood loss assessment is critical to the health of the subject, but currently is assessed by only crude techniques associated with the counting of saline units employed during the surgical procedure by the attending health care professional/anesthesiologist. At the conclusion of the surgery, typically the anesthesiologist will estimate the amount of blood lost by determining what volume of saline was used during the surgery overall, and then subtracting this saline volume from the total volume of mixed material collected in the collection canister(s).

Blood is composed of RBCs, and RBCs require a significant amount of time (over 3-6 hours) to settle out of a blood/fluid mixture collected at the time of surgery. Apart from the significant time required to provide even a reading of settled RBC volume, it has been found that the settled RBC volume does not provide an adequate approximation of blood volume for assessing blood needs. Current techniques for estimating blood loss are fraught with challenges, including human error (counting "used" saline bags, accounting for residual saline) and serious time constraints associated with conventional blood-containing fluid analysis.

Failure to accurately approximate blood loss during a surgical event results in a number of potentially serious health complications to the patient, as well as increased medical costs. For example, underestimation of blood loss can result in failure to provide a needed blood transfusion to the subject. This in turn results in the subject, in many cases, becoming anemic, requiring extended hospitalized to stabilize the patient and/or even death. An over estimation of blood loss may result in unnecessary blood transfusions and/or other unnecessary medical interventions, as well as in waste of blood units. Such may also cause increased risk of disease transmission (for example HIV, hepatitis).

The medical arts remain in need of improved techniques and materials to accurately estimate blood loss. Methods for more accurately monitoring and approximating blood volume in a fluid are needed. Fluid collection products suitable for providing a more accurate blood volume approximation are also needed, as will serve to reduce medical costs associated with unnecessary medical treatments and interventions that occur as a result.

SUMMARY OF THE INVENTION

In a general and overall sense, the present invention provides materials, devices and methods for more reliably and accurately approximating blood volume in a liquid, especially in a liquid collected during a surgical procedure.

Within this disclosure, it should be understood that the characterization of red blood cell (RBC) volume separated from a fluid containing blood plasma, saline or any other fluid (e.g., urine), does not mean an absolute or total separation, but instead an approximation of the stable sedimentation of RBCs in the fluid. RBC sedimentation is to be assessed at room temperature, and relates to the settlement of RBCs in a sample liquid by gravity (no centrifugation).

Methods of Approximating Blood Volume in a Liquid. In one aspect, methods for measuring blood loss from a mammal, such as a human or veterinary animal, using a RBC flocculant, are provided. The method in some embodiments comprises providing a liquid in a container having therein a RBC flocculant, wherein the RBC's within blood contained in the liquid will sediment to permit a visual and essentially simultaneous RBC sedimentation volume. While settled RBC volume does not equate to blood volume in a liquid, the RBC sedimentation volume is used to approximate blood volume in the liquid. The method employs a RBC sedimentation volume observed in the presence of a RBC flocculant, the aspect ratio of the collection device and an average hematocrit, to provide a visually ascertainable approximation of blood volume in the liquid. The visually ascertainable approximation of blood volume in a liquid/fluid containing or possibly containing blood using the present devices and methods may be achieved in less than an hour, and as quickly as within 15-30 minutes, using the techniques described herein. The very short time frame facilitated for providing RBC sedimentation in the presence of an RBC flocculant, and the consequent visual assessment of approximate blood volume, provides significant advantages in maintaining the well-being of the patient, as well as significant resource savings to the health care provider.

The methods may also be used to detect the presence of blood in a liquid, and in this manner, may be used to test a material (such as food materials, water, pharmaceuticals, etc.) for the presence of blood contamination. The material in question would be placed in contact with the RBC flocculant described herein, and examined for presence of RBC sedimentation. RBC sedimentation would indicate the presence of blood in the material.

Blood Indicator Panel. In some aspects, a Blood Indicator Panel (BIP) having defined demarcations calibrated to correlate with an approximation of blood volume in a fluid containing or suspected to contain blood is provided, as well as methods for preparing a BIP specific for blood from a particular mammal (human/non-human). Specific collection devices associated with the defined BIP are also presented.

The BIP may be used in conjunction with any conventional fluid collection devise and/or collection bag, in the presence of an RBC flocculant, to provide an approximation of blood volume in a fluid. The BIP employs a calculation that incorporates an estimated average hematocrit of the blood type being assessed as well as a device packed RBC volume determined for a collected fluid containing blood. A BIP is specifically provided for veterinary (equine, bovine, canine, feline) human and human uses (adult, infant). Reference to the BIP provides an efficient manner (without need for performing individual calculation) for estimating blood volume in a mixed fluid/liquid by cross-reference to settled RBC volume on a collection device. In some embodiments, the BIP may be used without conventional volumetric measures, and include only the calibrated blood volume markings for identification of blood volume in a liquid. In such cases, the type of blood and device has been pre-calibrated to provide approximated blood volume measures without reference to settled RBC levels.

RBC Flocculants and RBC Flocculation in a Fluid/Liquid. In one aspect, particular flocculants are identified that are suitable for flocculating RBCs, and thereby facilitate the sedimentation of RBCs by gravity. Combined with a biological fluid, such as the aspirate or other surgical run off collected during a surgical or other medical procedure episodes, the RBC flocculant will facilitate the rapid sedimentation of RBC's within a mixed fluid, such as within about 15 to about 30 minutes, compared to several hours that would otherwise be required for RBCs in a fluid to settle in the absence of a RBC flocculant.

As used in the description of the present invention, flocculation is defined as the coalescence or formation of clusters of RBCs, within a fluid comprising blood or potentially comprising blood. The methods may therefore be used to detect blood contamination, as well as to quantify an amount of blood in a material by providing for the detection of RBCs in the material and approximately blood volume according to the methods disclosed herein.

Fluids potentially comprising blood include saline, surgical aspirate, urine, bile, other biological waste materials, saliva, tissue preparations, digestive fluids, cerebral fluids, lymph, peritoneal fluid, amniotic fluid, and any mixture or combination of these. In this regard, virtually any moiety or chemical agent that is capable of promoting the coalescence of RBCs within less than about 30 minutes at room temperature to provide a stable settled RBC level, is considered useful as a RBC flocculant for purposes of providing the present devices and for use in the present methods. It is envisioned that virtually any moiety or chemical entity that may impart a positive surface charge to a negatively charged RBC would be useful to promote a more rapid coalescence, or flocculation, of RBC's together sufficient to enhance the speed of RBC sedimentation as part of the present devices and methods.

RBCs present in a fluid containing blood become bound to each other in the presence of an RBC flocculant, and in this manner form heavier particles that settle within the container/bottle/tube/collapsible bag or other vessel within which a sample/material is collected. Once the RBCs settle, the volume of the settled RBCs is recorded and employed together with a predetermined hematocrit of the mammal (animal/human), and a calculated RBC packing ratio associated with the collection vessel, so as to provide a real-time estimate of approximate blood volume in a liquid or mixed collected specimen.

In some embodiments, the flocculant is polydiallyldimethylammonium chloride (PolyDADMAC). Virtually any material or chemical may be used as a RBC flocculant in the practice of the present invention, as long as the material is able to facilitate the aggregation of RBCs to one another and decrease the time the RBCs aggregate and form a stable sedimentation level, preferably within about 15 minutes. The amount of RBC flocculant should be sufficient to facilitate the stable sedimentation of RBCs present in a fluid within less than about 60 minutes. In some embodiments, the amount of RBC flocculant should be an amount sufficient to facilitate a stable sedimentation of RBCS in a fluid within about 5 minutes, about 10 minutes, about 15 minutes, about 20 minutes, about 25 minutes or within about 30 minutes, or within a time range of about 5 minutes to about 20 minutes, at room temperature and in the absence of centrifugation. The amount of the RBC flocculant should be sufficient to impart a cationic charge to surfaces of RBCS in a liquid, such as a liquid comprising blood.

Molecules and materials for use as an RBC flocculant include polymeric RBC flocculants and non-polymeric RBC flocculants. For polymeric RBC flocculants, the RBC flocculant should have a molecular weight of at least about 100,000 Da, or about 200,000 Da, 300,000 Da or 400,000 Da, or a mixture of these, and have a relatively positive charge. By way of example, the polymeric RBC flocculants may include PEI, PAM, poly (acrylamide-co-acrylate), or any other relatively high molecular weight (greater than or equal to about 1,400,000 Da), positively charged polymer capable of imparting a positive charge to the surface of a RBC. Non-polymeric RBC flocculants may include acids, such as HCl or other acid molecule.

Other suitable high molecular weight cationic polymer RBC flocculants may be prepared by polymerization, such as by vinyl addition polymerization of one or more cationic monomers and by copolymerization of one or more cationic monomers with one or more cationic monomers. While cationic polymer RBC flocculants may be formed using cationic monomers, it is also possible to react certain non-ionic vinyl addition polymers to produce cationically charged polymers. Polymers of this type include those prepared through the reaction of polyacrylamide with dimethylamine and formaldehyde to produce a Mannich derivative.

The RBC flocculant may be used in solid form, in an aqueous solution, as a water-in-oil emulsion, or as a dispersion in water. Representative cationic polymers that may be employed as an RBC flocculant include copolymers and terpolymers of (meth) acrylamide with dimethylaminoethyl methacrylate (DMAEM); dimethylaminoethyl acrylate (DMAEA); diethylaminoethyl acrylate (DEAEA); diethylaminoethyl methacrylate (DEAEM); or their quaternary ammonium forms made with dimethyl sulfate, methyl chloride, or benzyl chloride. In alternative embodiments, the RBC flocculant may comprise dimethylaminoethylacrylate methyl chloride quaternary salt-acrylamide copolymers, sodium acrylate-acrylamide copolymers and hydrolyzed polyacrylamide polymers.

After RBCs are settled within a collection device or in a collapsible bag designed to conform to the dimensions of a collection device including an RBC flocculant, a settled RBC volume can be estimated using graduated markings on the collection device and/or collapsible bag that have been calibrated to provide a blood volume approximation. A packing ratio η may be determined, which is calculated using the settled RBC volume verses the RBC volume after centrifugation. With the determination of packing ratio, a total blood volume, such as a blood loss volume ($V_b$) or total amount of blood in a collected fluid, in the collection device can be estimated with the settled RBC volume ($V_m$), the subject's hematocrit (Hct) value (or an average HCT determined from a number of similar subjects), and the packing ratio q, according to the following formula:

$$V_b = V_m/(Hct \times \eta) \qquad 1)$$

Normally, in the absence of a flocculant, the RBC sedimentation rate, or erythrocyte sedimentation rate (ESR) is relatively low, or not detectable to the unaided eye (See FIG. 18). It may take many hours or even days for RBCs to settle within a collection container without centrifugation at room temperature in the absence of a flocculant. While not intending to be limited to any particular mechanism of action, this may be due, at least in part, to the electrostatic repulsive forces that naturally exist between RBCs, as RBCs are naturally negatively charged. In the presence of an RBC flocculant, such as the RBC flocculant polyDADMAC, the RBC settlement rate increases significantly. In the presence of an RBC flocculant, RBC sedimentation occurred in less than about 20 minutes, and formed a stable RBC sedimentation volume that was readily visible to the unassisted eye. The RBC sedimentation volume was considered sufficiently stable for purposes of the present methods when an observable change in RBC sedimentation volume was less than about 0.5% per minute.

Canisters, Collection Bags and Containers: Collection devices including canisters, collection bags and containers suitable for the collection and visual estimation of blood loss are provided. The collection devices may take the form of a round, square, octagonal, cylindrical, conical or virtually any configuration. The collection device should be sufficiently transparent or at least opaque so as to permit the visual detection of a level of material, such as sedimented RBCs, within the collection device. The collection device can be of a solid or flexible material, such as a hard plastic or glass, or a plastic material. The collection device may include a series of volumetric demarcations associated with the volume of the device itself, and an amount of an RBC flocculant suitable for facilitating RBC flocculation. The RBC flocculant may also be described as having a molecular weight sufficient to permit the settling of RBCs associated with the flocculant without centrifugation and at room temperature, within less than 30 minutes, or within about 5 minutes, about 10 minutes, about 15 minutes, or even about 20 minutes. The RBC flocculant may be provided in the collection device as a dry weight amount of flocculent, or as an amount of flocculent in a carrier solution, or as a pre-coating on the collection device (such as evenly coated on at least one surface, the entire surface, on a partial area, or as a strip along the inside of the device). These descriptions are provided by way of example and are not intended to provide limitation of potential embodiments envisioned for use and practice of the present devices and methods.

The following list presents an exemplary description of the treated and/or flocculant containing collection containers presented:

1,200 ml container (having a canister configuration), 5 ml and/or 10 ml graduated markings, one or more inlet ports, and one or more outlet ports (suitable for attachment of a tube suitable for imparting a suction so as to draw a fluid into the receptacle through a tube at the first inlet port).

500 ml container (having a canister configuration), 1 ml and/or 5 ml graduated markings, one or more inlet ports, and one or more outlet ports (suitable for attachment of a tube suitable for imparting a suction so as to draw a bio fluid into the receptacle through a tube at the first inlet port).

100 ml, 250 ml or 500 ml container(having a canister or conical configuration), 1 ml and/or 5 ml graduated markings), one or more inlet ports, one or more outlet ports, where at least one inlet port is suitable for attaching a tube for applying suction and drawing fluids and other materials into the container. These devices are particularly applicable for pediatric uses and smaller surgical procedures (sinus surgeries).

500 ml collapsible envelope (having 1 ml and/or 5 ml graduated markings, 1 or 2 inlet ports (resalable), and one or more outlet ports suitable for attachment of a tube suitable for imparting a suction to draw a fluid into the receptacle through a tube at the first inlet port).

100 ml, 200 ml, 250 ml, 300 ml, 400 ml, 500 ml, 1,200 ml, and 2,500 ml volume collapsible envelope (optionally having 5 ml and/or 10 ml graduated markings), 1 or 2 inlet ports (resealable) and one or more outlet ports (suitable for attachment of a tube for connecting the bag to a vacuum device, so as to draw a fluid into the receptacle through a tube at the first inlet port) (FIG. 13). The collapsible bag should be prepared from a plastic material, similar to that of a saline bag container, and will contain a suitable amount of a flocculant, such as polyDADMAC. The collapsible bag will also include a handle or other loop (FIG. 13, #10), located at one end to facilitate the hanging of the bag onto a mounting, such as an i.v. pole. A BIP may also be included on the bag, or may be placed as an attachment to the bag, which will provide a visually identifiable approximated measure of the volume of blood contained in a collected fluid. The bag may also include conventional volumetric markings, as are typical for saline and feeding bags.

100 ml, 250 ml and 500 ml conical collection receptacle (optionally having 1 ml, 5 ml, and/or 10 ml graduated markings), an RBC flocculant, 1 or 2 inlet ports (resealable) and one or more outlet ports (suitable for attachment of a tube suitable for imparting a suction so as to draw a fluid into the receptacle through a tube at the first inlet port). These smaller collection devices have particular applications and provide greater accuracy for smaller (less than about 500 ml) blood volume monitoring. These smaller devices, and/or collapsible bags designed to fit within them that include calibrated blood volume markings specific for the conical receptacle size, are useful especially in neonatal, pediatric and other critical surgical situations.

Method of Estimating Blood Volume and Blood Loss in a Fluid: In another aspect a method of estimating blood volume in a liquid is provided. In particular embodiments, the method is used to estimate blood volume loss from a patient from fluid collected during a surgical procedure.

The method includes collecting a volume of liquid into a collection device that includes a RBC flocculant suitable for imparting a relatively positive charge to the surface of a RBC, for a period of time sufficient to permit RBC sedimentation by gravity within the collection device. The volume of sedimented RBCs after a sufficient period of time, together with an estimated hematocrit of the type of animal/human blood in the fluid, is used together with a calculated RBC packing ratio determined for the particular collection device, to calculate an approximate blood volume value in the liquid collected, using Equation 1 above. Alternatively, these calculations are provided in a calibrated marking panel called a Blood Indicator Panel (BIP), as part of the present invention, which may be included on a blood collection device. As such, an immediate and visual blood volume assessment may be provided as RBCs in fluid collected in the flocculant containing collection device sediments. In some embodiments, the BIP will include a calibrated marker coinciding to an estimated blood volume of 50 ml, 100 ml, 200 ml, 400 ml, and 600 ml, and a volumetric alignment marking for aligning the BIP within a conventionally volumetrically marked fluid collection device (every 5 ml, 10 ml, for example), such as is common on a conventional 1200 ml canister.

Blood Volume Assessment System: Fluid collection Canister and/or Envelope and Tubing System: The invention also provides a kit that will include any one or more of the above receptacles including an appropriate amount of an RBC flocculant and calibrated with blood volume demarcations, a first length of tubing suitable for aspirating a fluid from an area into a first port on the receptacle, a second length of tubing suitable for connecting with a source of suction and a second port of the receptacle, so as to impart a vacuum in the receptacle. The system may be provided as a kit, and may also include an instructional insert.

BRIEF DESCRIPTION OF THE DRAWINGS

FIG. 3A—Settlement Volume Change with Time (30% blood in saline) the change in RBC sedimentation volume over time for blood/saline mixture sample with 30% blood concentration. FIG. 3B—Settlement Volume Change with Time (40% blood in saline). The change in red blood sedimentation volume over time for blood/saline mixture sample with 40% blood concentration. FIG. 3C—Settlement Volume Change with Time (65% blood in saline). The change in RBC sedimentation volume over time for blood/saline mixture sample with 65% blood concentration. FIG. 3D—The set-up of the experiment to measure the average RBC sedimentation volume over time. 1—Glass graduated cylinder, 2—sedimented RBCs (gravity), 2—total fluid level.

FIG. 5A-5B. 5A—Operating room with a collection canister (8) having a flocculant and a cap (15) on an i.v. pole (6), the cap (15) having an aspiration port (2), an inlet port (4) and a vacuum port (11). The inlet port (4) may be used to add saline or other diluent to the collection canister as needed. The collection canister (8) may include a blood indicator panel (BIP) (5). The aspiration port (2) will receive a tube (1) that is used to aspirate biological fluids away from an operating field during a surgical procedure of a patient (7). 5B—The collection canister (8) will include a cap (15) having an aspiration port (2), an inlet port (4) and a vacuum port (11). Aspirated fluids from a patient will be evacuated into the collection canister (8) by way of a suction being pulled on the collection canister through the vacuum port (11).

FIG. 10A—200 ml; FIG. 10B—400 ml; FIG. 10C—800 ml; and FIG. 10D—1200 ml, respectively. (Note: the volume measurements on each chart are obtained from the markers prepared for the 1200 ml canister treated with flocculant. Markers as part of a blood indicator panel (BIP) were provided to express an approximation of blood volume. It is estimated that the markers provide an approximation of blood volume (not settled RBC volume), that may vary as much as about 20 ml.).

FIG. 11 A. A stable settlement of RBCs was observed at 10-15 minutes in the 20% bovine blood/saline mixture in the polyDADMAC (flocculant particles, 10) coated 1200 ml canister (1). The settled RBC volume in the canister was observed at a volume level of about 110 ml. (2), and a total volume of 950 ml (3) according to the volumetric graduations on the canister.

DETAILED DESCRIPTION OF THE PREFERRED EMBODIMENT

Figure 1:
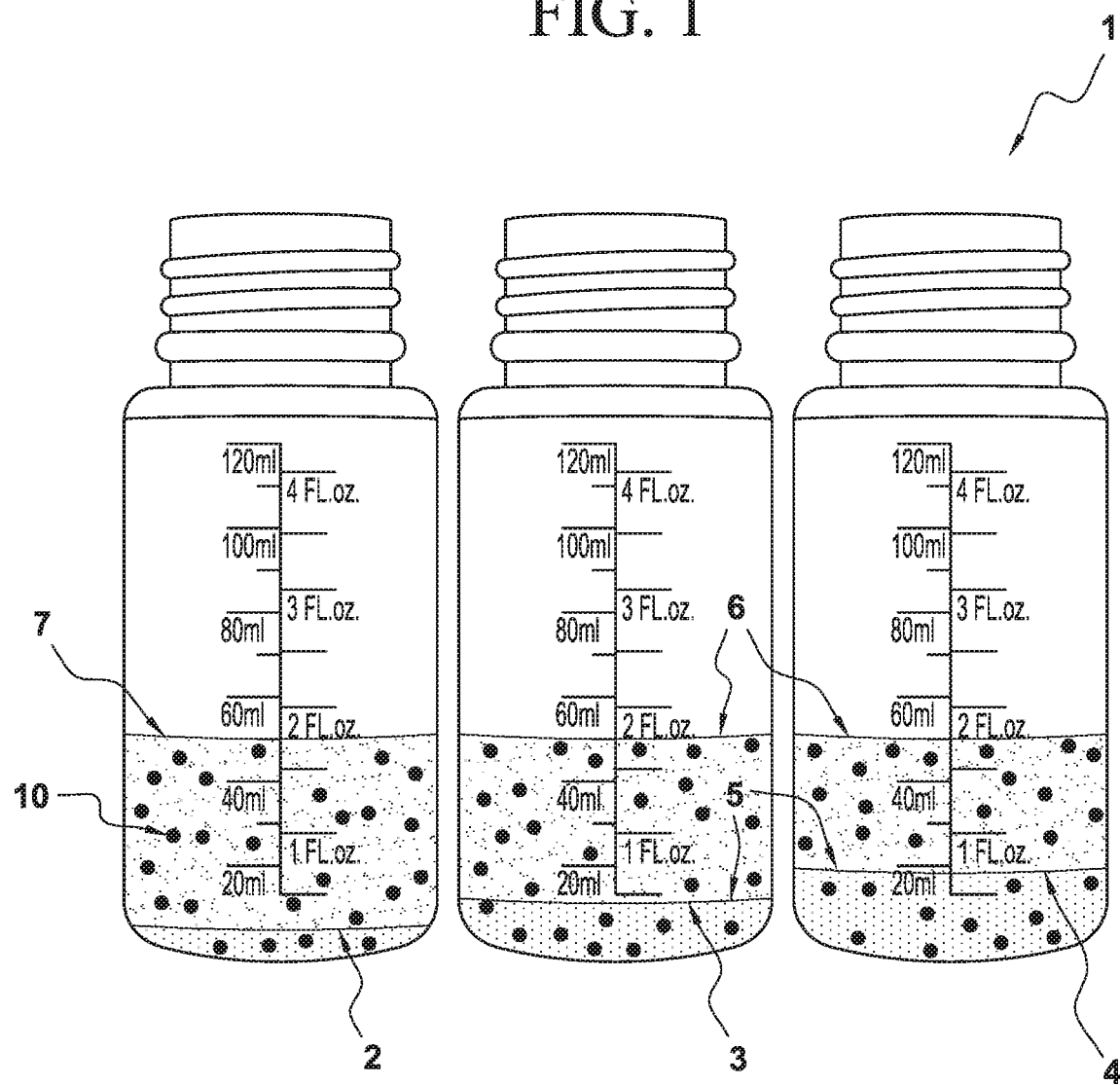
FIG. 1. 50 ml of 20%, 40%, and 65% bovine blood mixed with 200 ul of a 3× diluted Superfloc C-591 stock solution. 1—collection canister, 2—level of settled RBCs (by gravity), 3—level of settled RBCs (by gravity), 4—level of settled RBCs (by gravity), 6—total fluid level in canister, 7—total level in canister, 10—flocculant.

Unless defined otherwise, all technical and scientific terms used herein have the same meaning as commonly understood by one of skill in the art to which the disclosure pertains. Although any methods and materials similar to or equivalent to those described herein can be used in the practice or testing of the present technology, the preferred methods and materials are described herein.

As used here, the term "flocculant" is intended to mean a molecule that has a cationic charge that is capable of facilitating the coalescence of RBCs in a fluid at room temperature, and form a settled RBC mass with less than 30 minutes at room temperature without centrifugation.

Reference to an element by the indefinite article "a" or "an" does not exclude the possibility that more than one element is present, unless the context clearly requires that there be one and only one element. The indefinite article "a" or "an" thus usually means "at least one."

As used herein, "patient" or "subject" means an individual having symptoms of, or at risk for, cancer or other malignancy. A patient may be human or non-human and may include, for example, animal such a horse, dog, cow, pig or other animal. Likewise, a patient or subject may include a human patient including adults or juveniles (e.g., children). Moreover, a patient or subject may mean any living organism, preferably a mammal (e.g., human or non-human) from whom a blood volume is desired to be determined and/or monitored from the administration of compositions contemplated herein.

As used herein, "about" means within a statistically meaningful range of a value or values such as a stated concentration, length, molecular weight, pH, sequence identity, timeframe, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The following examples are presented to demonstrate preferred embodiments of the invention.

Example 1

RBC Flocculants

The present example presents materials that may be used as RBC flocculants in fluid containing or suspected to contain blood. The following chemicals in Table 1 may be provided as RBC flocculants.

TABLE 1

| Chemicals | Descriptions |
| --- | --- |
| Gelatin | A solution of electrostatic charged poly-peptides having a wide range of molecular weight. Literature indicates gelatin is able to increase RBC aggregation after adsorption on a RBC surface. |
| Dextran 80 + $CaCl_2$ | Literature indicates that Dextran 80 plus a divalent cation like $Ca^{2+}$ $Mg^{2+}$, and $Ba^{2+}$ will increase aggregation of RBCs |
| Acid Treatment | The isoelectric point of blood is at pH = 4.75-5. The pH change of blood samples to less than 4.75 will convert RBCs from negative to positive surface charge. |
| Polyethylenimine (PEI) with different molecular weight | PEI is a polymer composed of large number of positively charged amine groups, which is expected to attract RBCs to cause RBC settlement. |

TABLE 1-continued

| Chemicals | Descriptions |
|---|---|
| Polyacrylamide (PAM) with different molecular weight | PAM is widely used as a flocculants for water treatment. It can be configured to either positive or negative charge. Positively charged PAM is toxic to aquatic wildlife. |
| Aluminum sulfate (Alum) | Alum is positively charged at neutral pH. |
| Polydiallyldimethylammonium chloride (PolyDADMAC) with different molecular weight | PolyDADMAC is a positively charged water-soluble polymer |

Lab Test and Down Selection:

All the identified chemicals listed in Table 1 were tested and evaluated for suitability. Bovine whole blood purchased from Innovative Research (Novi, Mich.) was used to determine the suitability of each chemical above as a RBC flocculant. The whole blood contained with sodium citrate as the anticoagulant. The whole blood was diluted with saline to provide the following blood concentrations: 20%, 30%, 40%, 50%, 65%, and 80%, which were examined in the present studies.

Gelatin induced RBC aggregation but did not cause sedimentation. At the end, gelatin converted the entire blood/saline mixture samples into a gel structure. Without separating RBCs from the plasma and saline, gelatin is not suitable for this application.

Dextran 80+$CaCl_2$ also converted the blood/saline mixture samples into gels instead of separating the RBCs from the blood plasma and saline.

Acid treatments of the blood/saline mixture samples were performed by adding 1.8% of high concentration acid 6 N HCL. The pH of the samples was changed to about 4.5. The acid treatment caused aggregation and sedimentation of the RBCs. However, using relatively large amount of strong acid is not cost-effective for this application and it is difficult to handle strong acid in the process. Thus, acid treatment may be used to increase ESR.

PEI, a positively charged polymer, caused RBC sedimentation from the blood plasma and saline. The PEI must be dissolved under an acidic condition (i.e., with pH<7.0). In other words, a blood/saline mixture sample at neutral pH has to first have acid added to lower the pH before PEI can be used to facilitate RBC sedimentation in a biological fluid containing blood. The relative effectiveness of PEI and polyDADMAC were compared. The ESR (erythrocyte settling) induced by PEI was found to be lower than that of polyDADMAC. PEI is an acceptable flocculant for RBCs in a blood containing biological material (fluid).

PAM is a polymer that can be either negatively or positively charged. The negatively charged polymer will not induce the negatively charged RBCs to aggregate and settle. The positively charged PAM may be expected to be used for this application.

Alum is a positively charged molecule. It did facilitate a lower ESR, but at a much lower rate and amount. The relative molecular weight of a flocculant is considered for use as an appropriate flocculant because it enhances settlement of RBCs from gravity. In the studies with PEI and polyDADMAC, it was found that the higher molecular weight of those polymers caused faster RBC sedimentation.

PolyDADMAC is another positively charged polymer. It is also water soluble at neutral pH. PolyDADMAC in the presence of blood/saline mixture samples has the ability to rapidly cause RBC sedimentation. Only a small amount by weight of polyDADMAC is needed to induce the sedimentation. Quantitative studies are described below to determine the fraction of polyDADMAC needed proportionally to the amount of blood in a biological mixture containing blood. These studies also suggested that too great an amount of polyDADMAC may hinder, or even stop, RBC sedimentation. This may be because the RBCs become coated and surrounded by the positively charged polyDADMAC, and as such, the coated RBCs repel each other, by positive charges instead of negative charges, thereby hindering and/or preventing aggregation and sedimentation.

The low-cost, high molecular weight (at least 100 KDa, 200 KDa, 300 KDa or about 400 KDa), positively charged polyDADMAC was identified as a preferred, cost-effective flocculant to quickly induce RBC sedimentation. Other high molecular weight, positively charged polymer flocculants (e.g., PEI, PAM, etc.) would also be useful in the practice of the present methods and creation of container vessels. It is expected that an acid treatment would also be useful as part of the method to provide RBC sedimentation.

Example 2

Blood Loss Estimation

The present example demonstrates the material polyDADMAC as an effective flocculant for RBCs contained in a fluid, and the use of this flocculant for estimating total blood volume in a fluid that contains blood and other liquids, including saline.

High-molecular weight (at least 100, 200, 300 or 400 KDa) research-grade polyDADMAC was obtained from Sigma-Aldrich (Catalog number 409022 or 409030) along with industrial-grade polyDADMAC. The industrial-grade product is commercially available from Kemira Chemical under the product name "Superfloc C-591", which contains a 20% concentration of polyDADMAC. This material is used in water treatment. Studies were performed to compare the effectiveness between the research-grade and industrial-grade products. The studies revealed that the Superfloc C-591 produced similar results in RBC sedimentation as the research-grade product. The cost of the industrial-grade product is lower than that of the research-grade product. The purity of C-591 varied, resulting in some differences in RBC flocculation. In the use of research grade and industrial grade polyDADMAC, the 20 wt. % in water stock solutions were diluted with water to 6.67 wt. % working solution to reduce the viscosity of the solution and to enhance ease of handling. The dry weight of flocculant for a 1200 ml collection canister was about 600 mg. of polyDADMAC.

Amount of Flocculant Needed to Facilitate RBC Sedimentation. Superfloc C-591 (obtained from the manufacturer (viscous liquid, 20 wt. % in $H_2O$) was used as a RBC flocculant to test a bovine blood and saline mixture. The amount of flocculant needed to facilitate a more rapid RBC sedimentation rate was examined. It was discovered only about 0.4% (v/v %) of the Superfloc C-591 working solution added to the total blood/saline mixture volume was needed to provide an acceptably rapid (within 15 minutes) sedimentation of RBCs in the mixture. For example, in a 1-liter blood/saline mixture sample, only 4 ml of the Superfloc C-591 working solution was needed, regardless of the blood concentration in the mixture. This translates to about 320 mg of polyDADMAC flocculant for a 1.2 liter canister.

FIG. 1 illustrates three 50 ml-volume blood/saline mixture samples with the blood concentrations (from left to right in the figure) of 20%, 40%, and 65%, respectively. The addition of the same amount of 200 µl (or 0.4% of 50 ml) of the Superfloc C-591 working solution induced red blood sedimentation at all of these blood concentrations. However, the sedimentation rate was found to be different depending on the concentration of blood in the particular mixture, as discussed below.

Tests also revealed lower or higher concentrations of the Superfloc C-591 working solution may be used. For example, concentrations as low as 0.3% (v/v %) and as high as 0.6% (v/v %) were found effective, however, the exact upper and lower limits were not determined. It was found that a 6% (v/v%) concentration of the Superfloc C-591 working solution added to blood/saline mixture sample with a 20% blood concentration induced minimal settlement, but that may not be the upper limit for sedimentation.

Figure 2:
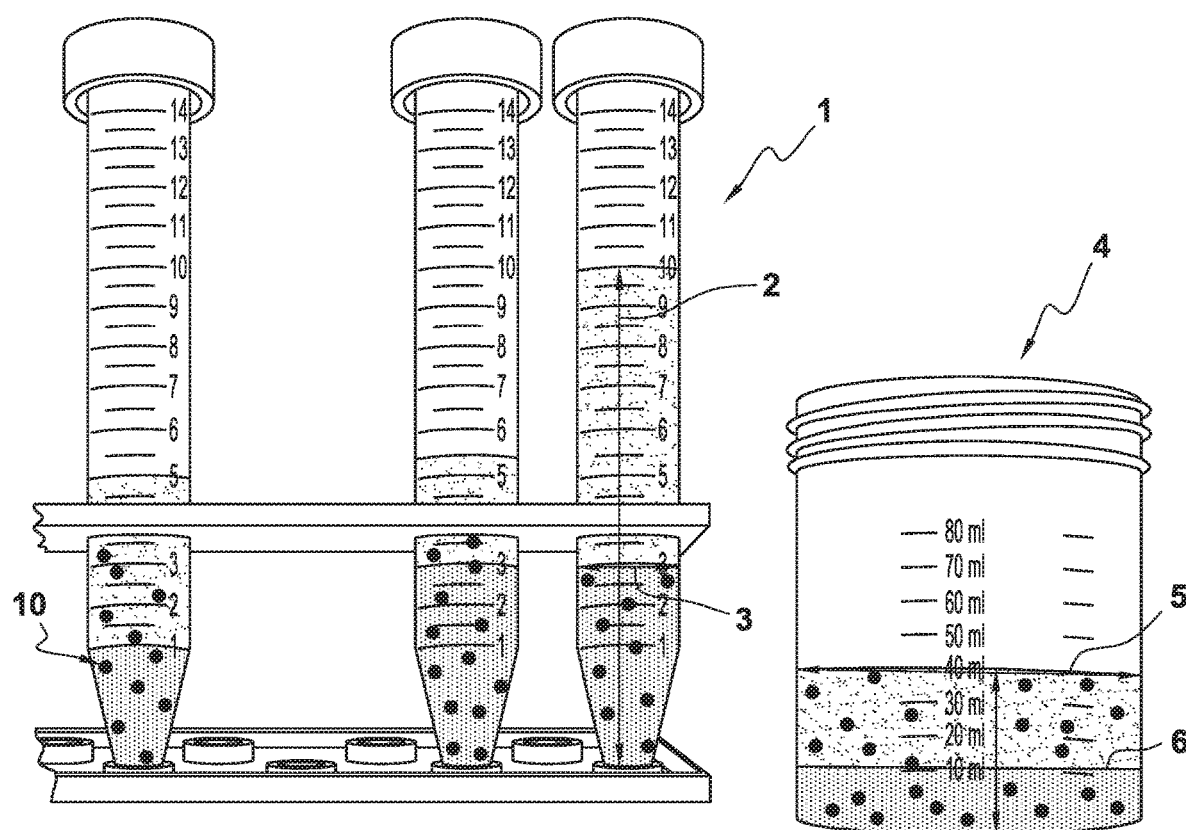
FIG. 2. Containers with different aspect ratios have different red blood sedimentation rates. 1—graduated conical tube, 2—graduations at 0.5 ml intervals on conical tube, 3—level of sedimented RBCs (gravity), 4—100 ml collection canister, 5—total fluid level in canister, 6—level of sedimented RBCs (gravity), 10—flocculant.

Aspect Ratio of Blood Container (Receptacle or Canister). During the experiments, it was found that the RBC sedimentation rate depends, in part, on the aspect ratio D: H of the container, where D is the diameter and H is the height of the container as shown, for example, in FIG. 2. The aspect ratio D: H depends on the shape of the container. The sedimentation rate is higher when D: H is higher because a larger D provides a larger area or space for the aggregated RBCs to settle by gravity. Therefore, the sedimentation rate will be different when different blood collection containers (or canisters) are used.

Another finding during the experiments is that the Superfloc C-591 flocculant sedimented RBCs if it is placed in the container before adding the blood/saline mixture samples as well as when added to the container after it is already filled with the blood/saline mixture samples.

Figure 3A:
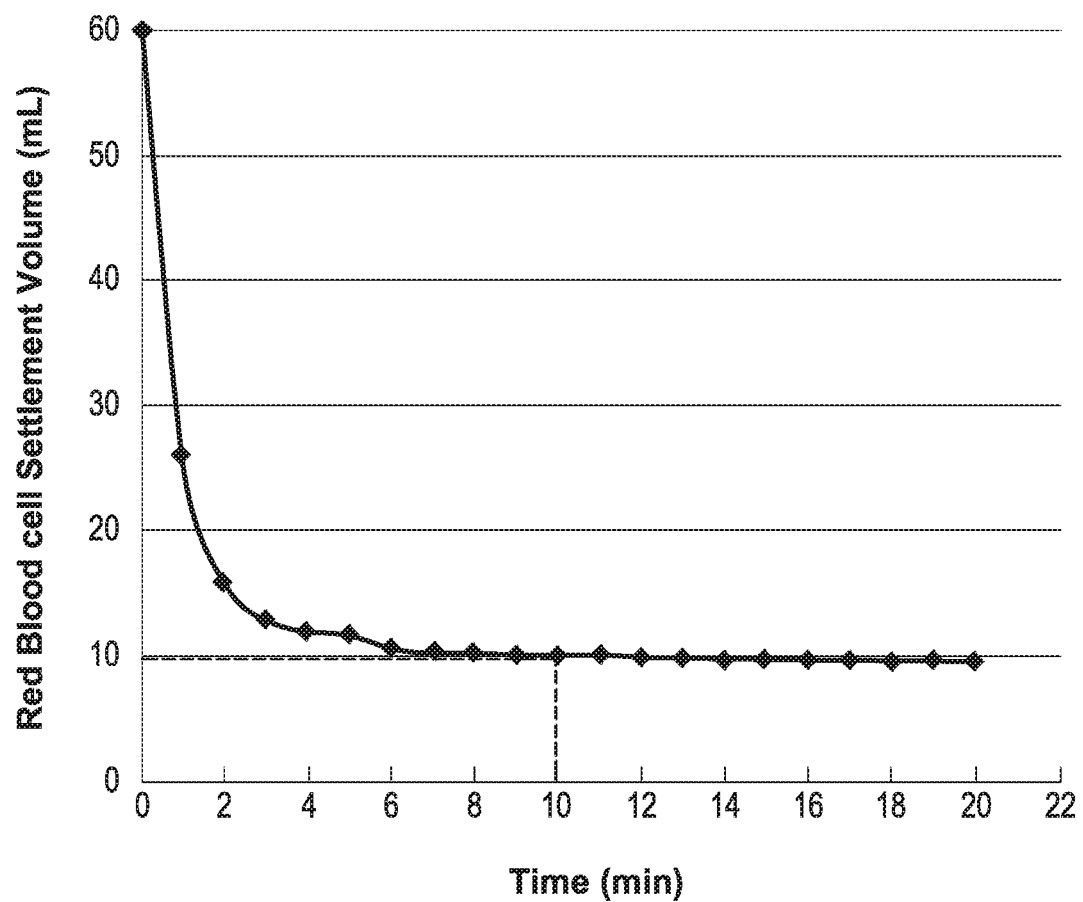
FIG. 3A-3D.
Figure 3B:
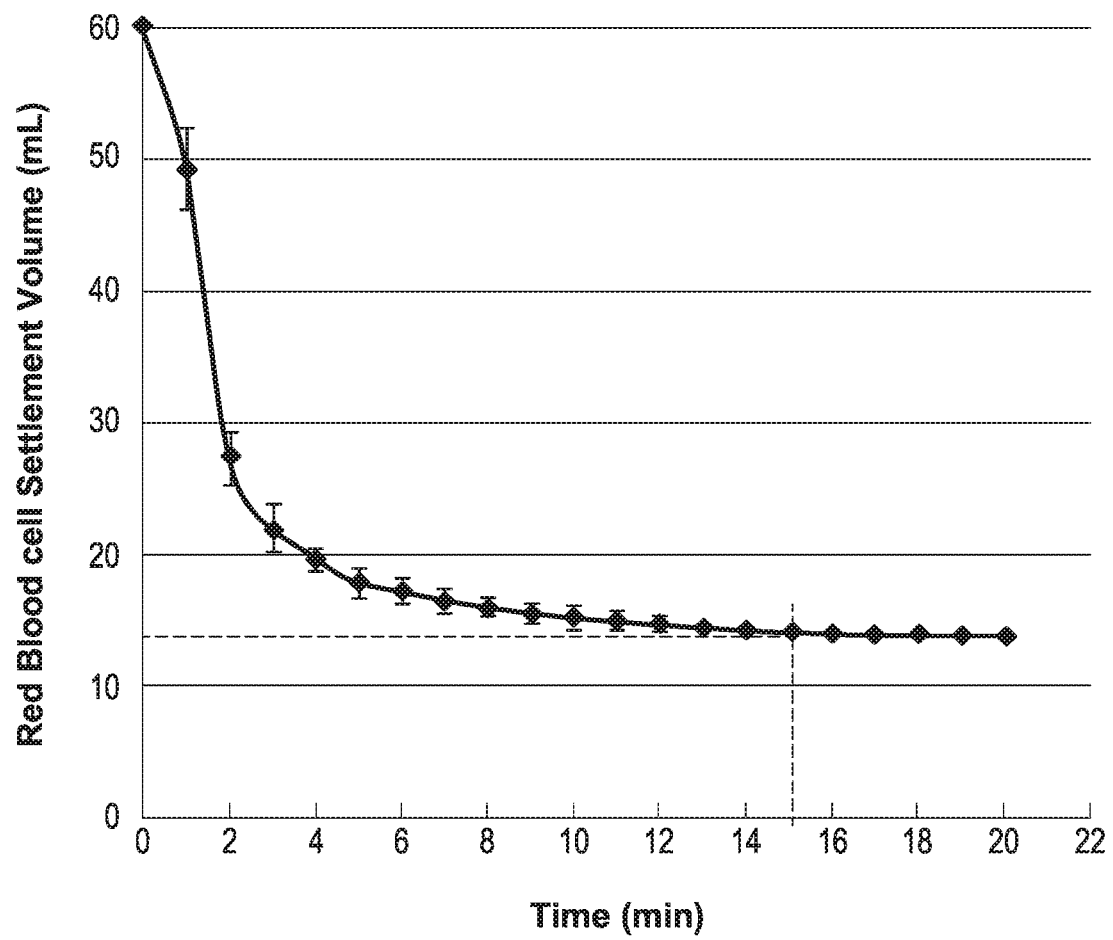
Figure 3C:
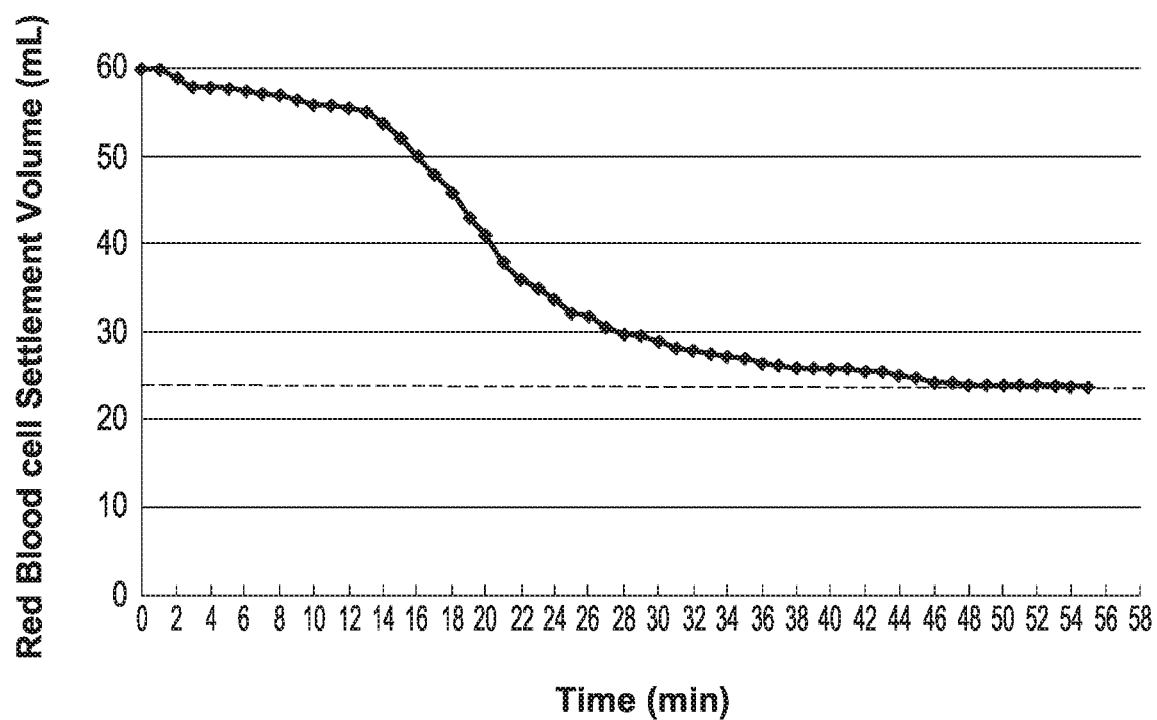

Sedimentation Rate and Blood Concentrations. The present studies indicated that the blood concentration in the blood/saline mixture also affects the RBC sedimentation rates, with a faster sedimentation rate in samples having a lower concentration of blood versus samples containing a higher concentration. FIGS. 3A, 3B, and 3C, for example, illustrate the sedimentation rates of the RBCs in the 30%, 40%, and 65% blood/saline mixture samples, respectively.

Figure 3D:
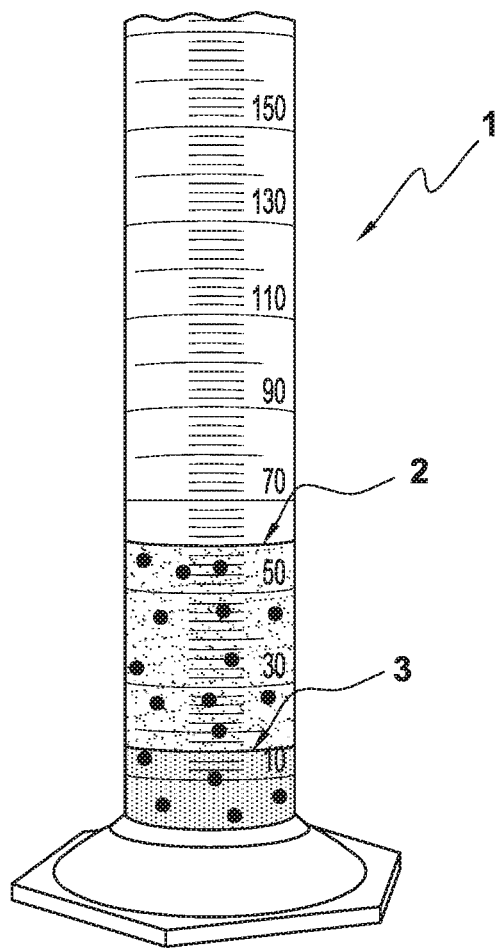

A graduated glass cylinder (FIG. 3D) was used in these studies to determine difference in the sedimentation rates. Three 60 ml blood/saline mixture samples, with blood concentrations of 30%, 40%, and 65%, were used in the experiments. A drop of 240 µL (or 0.4% of 60 ml) of the Superfloc C-591 working solution was added to the glass cylinder first. Then a 60 ml blood/saline mixture sample was added to the glass cylinder. The separation of the RBCs was visually observed by a clear differentiation of fluid layers within the glass cylinder, with the settling RBCs being the more opaque fluid layer toward the bottom of the cylinder and the blood plasma/saline layer being the clearer fluid layer above the settling RBC layer. The settled RBC volume within the cylinder was recorded by reference to the cylinder graduated markings and recorded every minute.

The settling RBC volume was set to 60 ml at time 0 since no visual separation had started at time 0. After time 0, the RBCs begin settling from the blood plasma/saline layer and initially settle toward the bottom of the container at a high sedimentation rate, but the sedimentation rate decreases over time. In this regard, as the amount of RBCs separated from the blood plasma/saline layer increases there are fewer RBCs to separate from the blood plasma and saline. Eventually, the RBC sedimentation rate is very low, so that the rate of RBC volume change is less than 0.5% per minute. At this point, the volume of settled RBCs is considered stable. In other words, a stable sedimentation is achieved when the volume change of the settled RBCs is less than 0.5% per minute. The "packed RBC volume," which is denoted as $V_m$, is the volume of the RBC layer at the bottom of the container when the RBC sedimentation is considered stable.

FIG. 3A illustrates that the blood/saline sample mixture with 30% blood concentration started RBC sedimentation almost instantly after mixing with the flocculant. Most of the sedimentation was complete within one minute. A stable RBC sedimentation was achieved around 10 minutes after the sample is mixed with the flocculant. The stable packed RBC volume $V_m$ was about 9.5 ml. For the blood/saline mixture sample with 40% blood concentration, the sedimentation rate slowed slightly (FIG. 3B). The most sedimentation of the majority of RBC's occurred at two minutes instead of the one minute observed for the 30% blood concentration sample. A stable sedimentation for the 40% concentration sample was achieved at about fifteen minutes and the $V_m$ is about 14 ml. For the 65% blood concentration sample, the sedimentation was slower. (FIG. 3C). It took over 60 minutes before a stable sedimentation was observed. The methods for determining blood volume in a blood/saline mixture were optimal and consistent in liquids containing 50% or less blood. Rapid sedimentation is characterized as achieving a stable sedimentation of RBCs in a saline/blood mixture within fifteen minutes of addition of the flocculant at room temperature (no agitation of the mixture during settlement).

Figure 4:
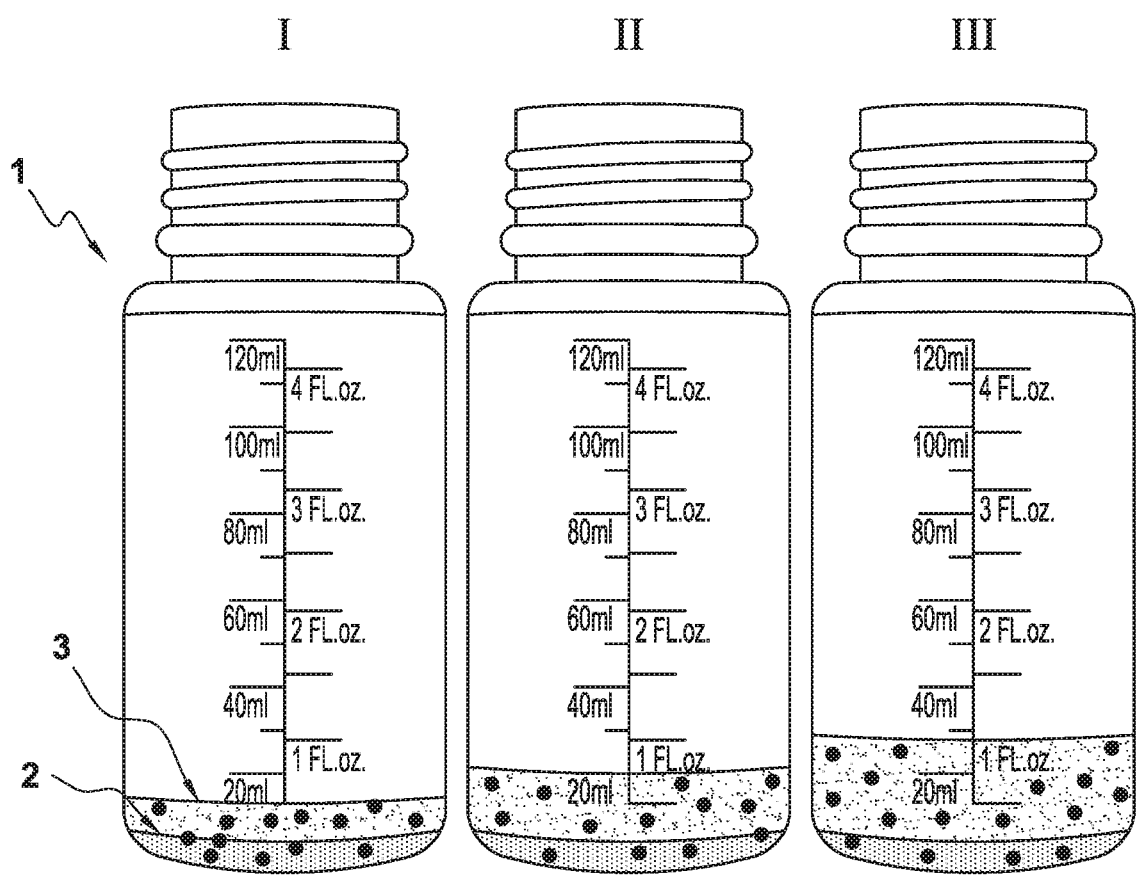
FIG. 4. The RBCs in 10 ml of 80% blood sedimented when diluted to 53.33%, 40% and 26.7%, respectively, with saline, going from left to right. All concentrations settled to the same packed RBC volume. 1—1200 ml collection canister with flocculant, 2—settled RBC level, 3—total fluid in canister.

To ensure that the blood concentration in a fluid remains below about 50%, blood (for optimal RBC separation), additional saline or other appropriate blood diluent may be added. It was found that blood/saline mixtures with high concentrations of blood can still achieve a rapid sedimentation. One way in which sedimentation may be reinitiated should the sedimentation rate appear to be slowing down, one may add an additional volume of saline so as to further dilute the blood. Three 10 ml blood/saline mixture samples with 80% blood (bovine blood containing sodium citrate anti-coagulant) concentration were prepared in three bottles, as shown in FIG. 4. All samples were mixed with 30 µL (about 0.3% of 10 ml) of the Superfloc C-591 working solution (about 2 mg dry weight Superfloc C-591). No sedimentation was observed before the samples were diluted. Each bottle had saline added to dilute the blood concentration and, going from left to right in FIG. 4, 5 ml, 10 ml, and 20 ml of saline was added, which diluted the samples to 53.3%, 40%, and 26.7%, concentrations of blood, respectively. The container was agitated slightly to mix the added saline with the sample. Upon dilution, the RBCs began to sediment.

The 26.7% blood concentration mixture and the 40% blood concentration mixture achieved a stable sedimentation at around 10 minutes. The 53.3% blood concentration mixture achieved a stable sedimentation at about 16 minutes. As shown in FIG. 4, the final packed RBC volume (i.e., the darker bottom layer at the bottom of the container) in all three samples is the same, even in the presence of different amounts of saline. This result was achieved because the initial 10 ml of 80% blood concentration mixture contains the same amount of blood volume, 8 ml. This study indicated that 1) more saline can be added to dilute a blood/saline mixture to help increase the RBC sedimentation rate and 2) the total blood volume can be estimated through the sedimentation of the RBCs, since the volume of RBCs aggregated at the bottom of the container (i.e., the packed RBC volume) is not affected by the amount of saline in a blood/saline mixture.

It should be noted that with other flocculants or other chemical treatments discussed above, further testing using the testing protocol previously outlined may be followed to determine optimal flocculant concentrations and blood/saline ratios.

Figure 10A:
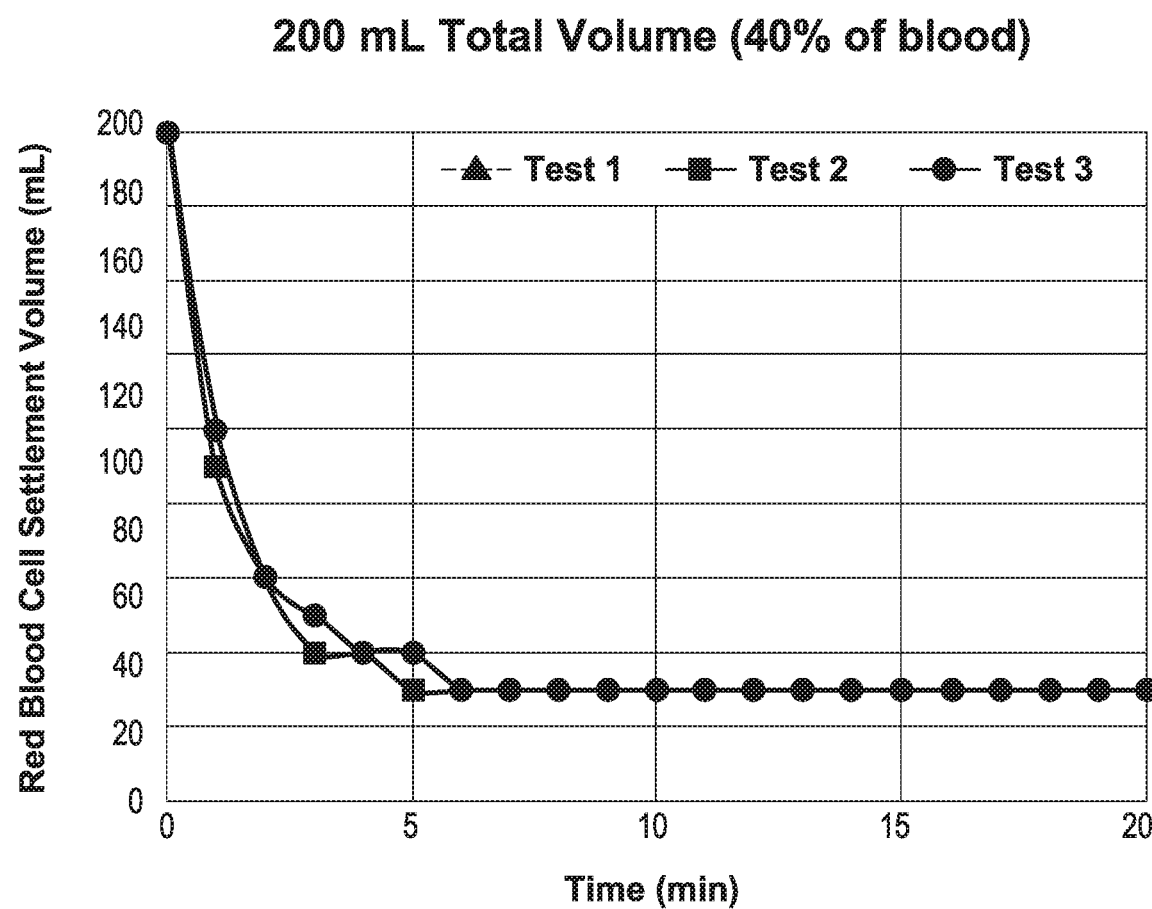
FIG. 10A-10D. The change of RBC settlement volume along a 20-minute time period with 40% blood/saline. The total blood/saline mixture volumes are.
Figure 10B:
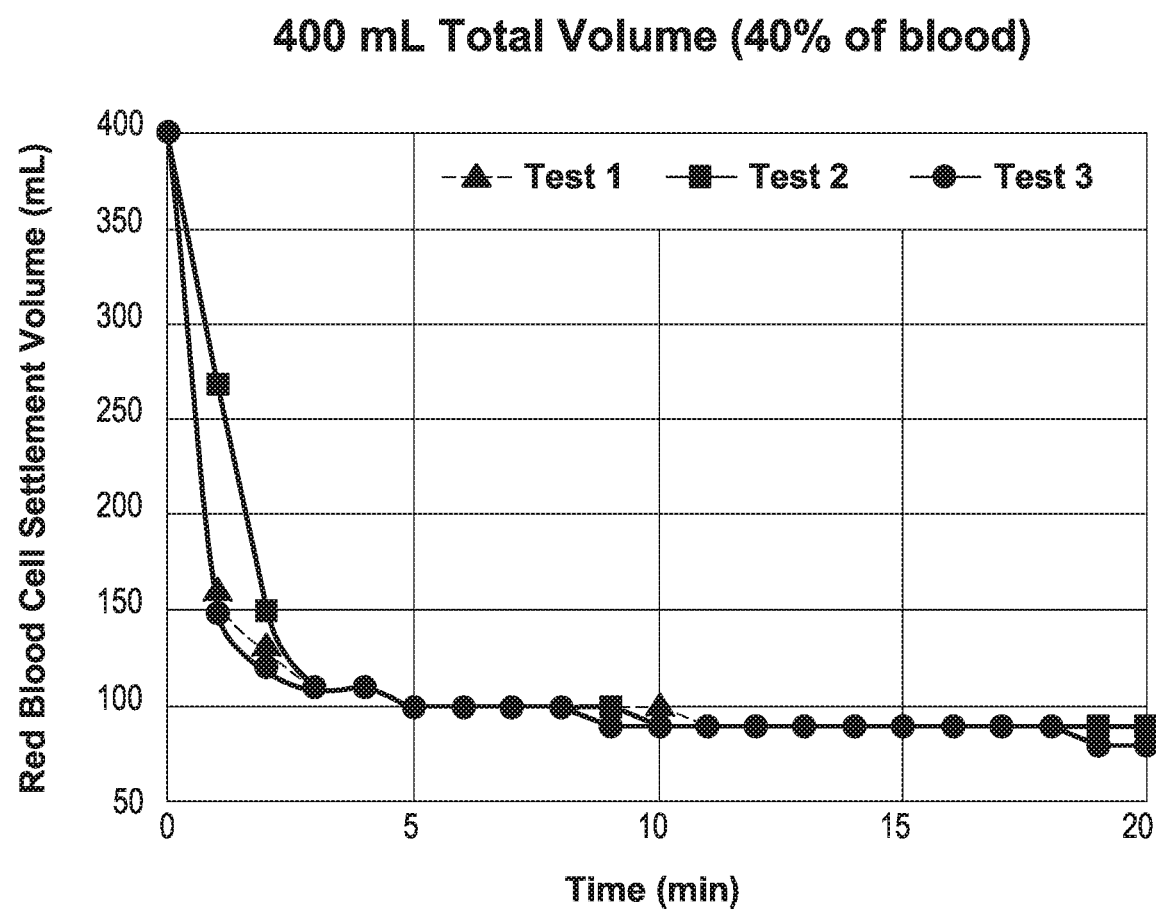
Figure 10C:
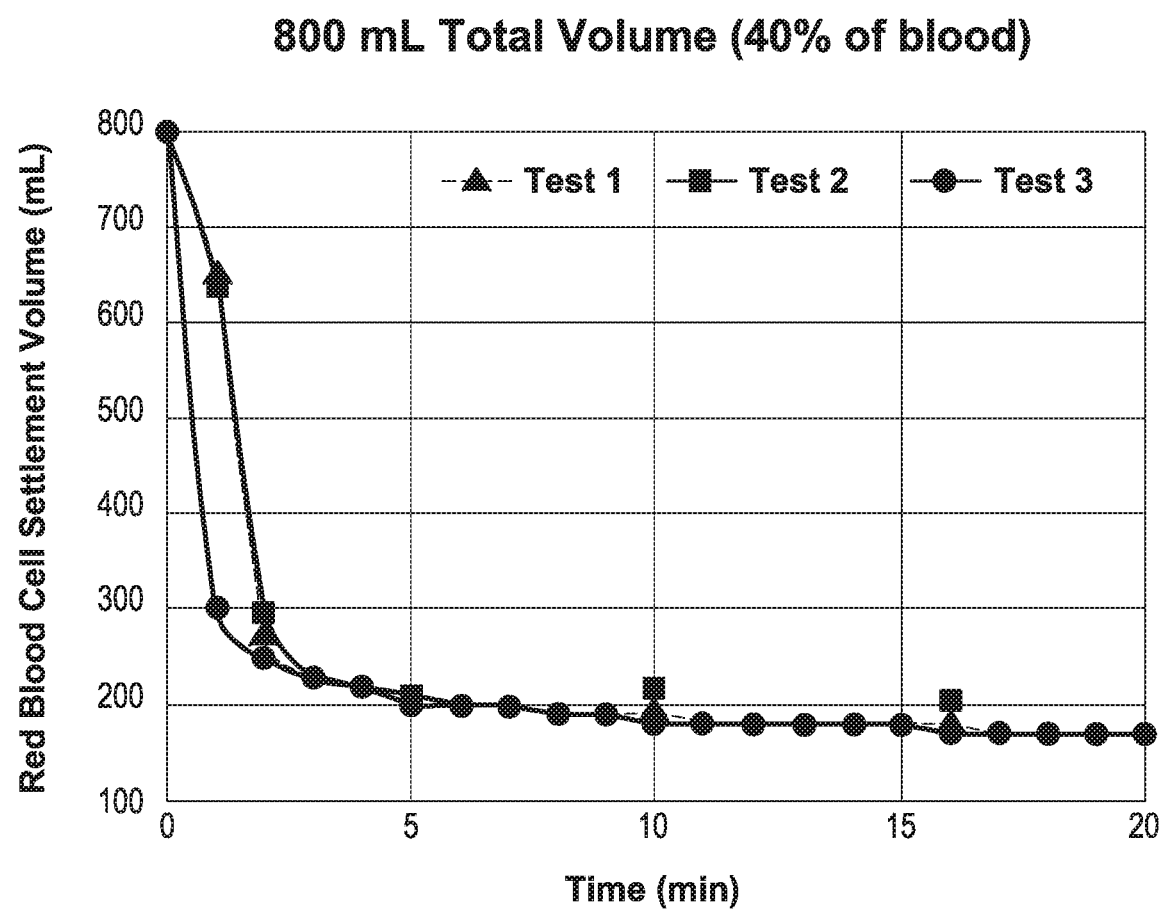
Figure 10D:
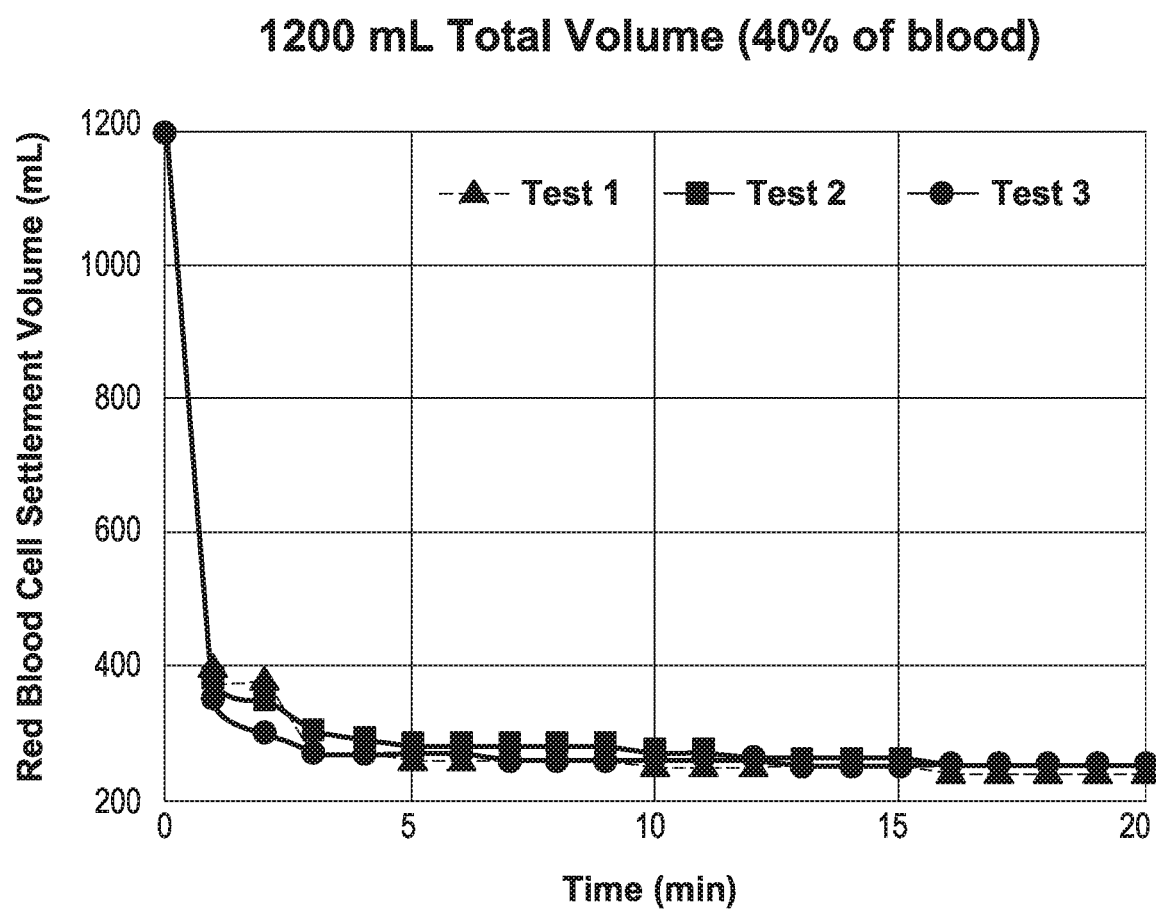

Repeatability. The RBC sedimentation study using the 40% blood (bovine blood with sodium citrate anticoagulant) concentration mixture (FIG. 10A) was repeated three times. Standard deviation error bars are shown at various points on the line in the FIG. 10A plot. The repeatability of the experiments was very good, especially at the points on the line when the sedimentation approaches stability. Relatively high variations occurred initially as shown by the longer standard deviation error bars at those points on the line, but these variations are probably due to visual reading errors caused by the rapidly changing volume of the settling RBC layer at those points. The data variation is very small when the sedimentation approaches stability. In other words, the variation of the packed RBC volume is small when the sedimentation is stable.

Total Blood Volume Estimation. To demonstrate the feasibility of estimating the total blood volume, an algorithm was developed to estimate the total blood volume in a blood/saline mixture based on the sedimented RBC volume $V_m$. If the actual RBC volume is denoted as $V_c$ (as determined through centrifugation), the total blood volume is denoted as $V_b$, and the patient's hematocrit is denoted as Hct, then the following relationships are created:

$$\eta = V_m/V_c, Hct = V_c/V_b \rightarrow Vb - V_m/(Hct \times \eta)$$

Since Hct is available from the patient data measured prior to surgery and $V_m$ is measurable based on the method described above, the total blood volume $V_b$ can be estimated when the value of the packing ratio ($\eta$) between $V_m$ and $V_c$ is determined experimentally beforehand (methods and examples are presented herein, demonstrating the method for determining packing ratio $\eta$).

The values of the packing ratio $\eta$ may be different for different blood types (e.g., human versus non-human). The packing ratio value is also likely to be container-specific in that it may vary according to the size and shape (aspect ratio) of the container used to collect the blood. In this regard, recall tests showed the container shape affected the ESR (Erythrocyte sedimentation rate). Thus, the packing ratio $\eta$ should remain the same where the same blood type and container shape for blood measurement are used.

The packing ratio $\eta$ is determined empirically by using a known hematocrit value and a known volume of blood within a blood/saline mixture. Preferably, the value of the packing ratio $\eta$ will be determined by finding an average packing ratio value from numerous blood/saline mixture samples with different known blood concentrations. In this regard, by running a study with blood from the same species of animal (bovine, equine, human), and a container having a defined size and shape, in the presence of the flocculant as described herein, where different known blood/saline concentration mixtures are examined, an appropriate packing ratio $\eta$ may be calculated. The greater the number of different blood/saline mixtures examined, the more statistically reliable the average packing ratio value derived will be. As discussed above, the blood concentration of a collected fluid in some embodiments should be about 50% or less blood. Additionally, an average hematocrit may be determined from a number of hematocrit values obtained from a representative number of subjects (animal/human). Hematocrit may be calculated using traditional capillary centrifugation methods, as known by those of skill in the art. The average hematocrit value for a group of animals, such as a group of humans or a group of horses, etc., will provide a value $V_c$ that can be used in the formulas and methods described herein when the blood volume is known during the particular collection episode.

As noted, the value of the packing ratio $\eta$ is preferably an average packing ratio value calculated from a group of blood/saline mixture samples in a defined collection container. The actual RBC volume $V_c$ and the settled RBC volume (by ordinary gravity, at room temperature), $V_m$, facilitated in the presence of an RBC flocculant, will be determined for a number of individual samples, and an average packing ratio value determined. To determine the actual RBC volume $V_c$, the hematocrit of the blood added to a mixture sample is multiplied by the volume of blood added to that sample.

Next, the packed RBC volume $V_m$ may be determined for each mixture sample using conventional volumetric graduated markings on a container, as described above. That is, with the flocculant present, the $V_m$ may be determined by reading the volume of the RBC sedimentation. As part of the method, the same type and amount (concentration in the total fluid mixture volume) of RBC flocculant should be added to a collection container. As shown in table 2, even when the flocculant, polyDADMAC concentration was changed, the packing ratio $\eta$, remained relatively consistent. Thus, a range of flocculant concentrations (range of flocculant of about 0.3%, 0.4%, and 0.75% flocculant in the total liquid volume) can be used to induce RBC sedimentation without significantly affecting the packing ratio. In addition, the data in Table 2 demonstrates that the packing ratio is relatively insensitive to the amount of blood volume in the liquid mixture (blood/saline), when the flocculant concentration remains relatively the same.

With the actual RBC volume $V_c$ and the settled, packed RBC volume $V_m$ for each mixture sample, a packing ratio value, $\eta$ value, for each sample (i.e., each different blood concentration mixture) can be determined. Then, an average packing ratio value may be calculated. For bovine blood, for example, the average packing ratio calculated was 1.61 (See Table 2).

To demonstrate the empirical determination of the packing ratio value, the value of the packing ratio $\eta$ was determined for bovine blood purchased from a commercial vendor, these blood materials containing sodium citrate (for anticoagulant). Plastic canisters that were marked for volume (ml) were used, and are shown in FIG. 4. The results are illustrated in the following table 2. Before the experiments, the average hematocrit Hct of bovine blood was calculated from a number of bovine blood samples, and determined to have an average of 37.3%. This average Hct is used in the table below, and was used in the present approximation of blood volume in a sample. A traditional capillary centrifugation method was used for determining individual Hct values.

TABLE 2

| Experiments | Hct | $V_b$ (ml) | $V_c$ (ml) | $V_m$ (ml) | η value |
|---|---|---|---|---|---|
| 30 ml 20% blood concentration + 90 μl flocculant (i.e., 0.3% (v/v %) concentration of polyDADMAC working solution (6 mg.) | 37.3% | 6 ml | 2.24 | 3.5 | 1.56 |
| 30 ml 40% blood concentration + 180 μl flocculant (i.e., 0.6% (v/v %) concentration of polyDADMAC working solution (12 mg) | 37.3% | 12 ml | 4.48 | 7.5 | 1.67 |
| 50 ml 20% blood concentration + 200 μl flocculant (i.e., 0.4% (v/v %) concentration of poyDADMAC working solution (13.3 mg) | 37.3% | 10 ml | 3.73 | 6.0 | 1.60 |
| 50 ml 40% blood concentration + 200 μl flocculant (i.e., 0.4% (v/v %) concentration of polyDADMAC working solution (13.3 mg) | 37.3% | 20 ml | 7.46 | 12.0 | 1.61 |
| Average | | | | | 1.61 |
| Coefficient of Variance | | | | | 2.8% |

The packing ratio values that resulted from these experiments showed relatively small variations. In these experiments, the blood concentration of all blood/saline mixture samples in the chart above is less than 50% since mixtures with a higher amount of blood can be diluted to provide a mixture with less than 50% blood by adding saline. After determining that the Hct is 37.3%, and the mean packing ratio η value equals 1.61, the total blood volume in a blood/saline mixture can be estimated using the following formula (derived from Equation 1):

$$V_b = V_m/(37.3\% \times 1.61) = 1.67 \times V_m$$

The number 1.67 in the above formula is the calculated value of the 1/37.3% (average Hct)×1.61. (average η value from Table 2).

The following Table presents a comparison between the actual blood volume known to be present in each sample compared to the approximate volume (in ml) of blood in the sample determined through the calculation of blood volume determined using the formula above and techniques described here. The results demonstrate that the formula and techniques provided here may be used to provide an approximation of blood volume in a liquid sample containing mammalian blood (for example, bovine blood), in the presence of a RBC flocculant (for example, a polymeric flocculant such as polyDADMAC). In addition, the data shows that the approximated blood volume present in a collected mixed blood/saline liquid sample closely correlates with the actual blood volume in the liquid.

TABLE 3

| Experiments | $V_m$ (ml) | Approximate $V_b$ (ml) | Actual $V_b$ (ml) |
|---|---|---|---|
| 30 ml 20% blood | 3.5 | 5.85 ml | 6 ml |
| 30 ml 40% blood | 7.5 | 12.53 ml | 12 ml |
| 50 ml 20% blood | 6.0 | 10.02 ml | 10 ml |
| 50 ml 40% blood | 12.0 | 20.04 ml | 20 ml |

The 20% blood noted in Table 2 is composed of 200 ml bovine blood and 800 ml saline in every 1000 ml of fluid mixture.

Example 3

Fluid Collection Canister

The present example demonstrates the preparation of a particular fluid collection container with a RBC flocculant. Blood Containing Liquid Collection Container. The fluid collection container used in the following examples was a 1200-ml suction canister, shown in FIG. 7B. To this canister (1), a flocculant was applied, polyDADMAC, which appears as a film of dispersed flocculant particles (2) on the bottom and walls of the canister.

Flocculant—PolyDADMAC. Kemira's "Superfloc C-591" was used as the source of polyDADMAC. The quality or purity of this product was not consistent. Therefore, the Sigma-Aldrich version of high-molecular weight (200-350 KDa) 20% polyDADMAC (Sigma Catalog # 409022) was used. The results indicate that the Sigma version of polyDADMAC significantly improve the testing results. However, it is anticipated that virtually any number of different sources flocculants may be used in the practice of the present invention, as well as in the fabrication of the herein described flocculant containing and treated fluid collection containers.

Example 4

Optimization of PolyDADMAC as the Flocculant for a 1200 ml Collection Canister for Blood Volume Approximation in a Mixture containing Blood In the operating room, a biological fluid waste collection canister may be used to collect a volume of fluid, which will include an unknown volume of blood. The volume of blood in a canister volume of 1200 ml can vary anywhere from 10 ml to 1200 ml. The volume of blood in a collected fluid collected may also vary depending on specific species of animal, the gender and weight of the patient, as well as the particular medical procedure, being performed. However, the volume of blood in a collected fluid in a collection canister during a typical adult human surgical procedure is generally contains about 20% to about 50% blood. Conventional techniques for blood volume determination used in a standard hospital operating settings provide only gross estimations of blood volume that are most times inaccurate by at least 50%-75%, and are not available until hours after a surgical procedure has been completed.

In most cases, the amount of blood in an aspirated fluid during a surgical procedure is 50% or less. In those cases where the fluid contains more than 50% blood, the present methods and devices may be used to accurately determine blood volume by adding saline or other diluent to the fluid to lower the blood concentration, so as to facilitate the sedimentation of RBC's in the fluid in the presence of a RBC flocculant, polyDADMAC.

The present example demonstrates that a relatively constant amount of RBC flocculant, such as polyDADMAC, may be used to achieve a relatively accurate estimation of blood volume is a fluid containing about 50% or less blood concentration. This is achieved by using a visual reading of the volume of settled RBCs in a calibrated canister containing a RBC flocculant. This volume of settled RBCs is then used in a calculation to determine the volume of blood in the mixture. The settled RBC volume value alone is insufficient to accurately approximate blood volume in a mixture.

A test of 40% of blood at three different volumes of a blood/saline mixture was tested. The volumes of 40% blood/saline mixtures tested were: 200 ml, 800 ml, and 1200 ml. A Sigma-Aldrich polyDADMAC (20 wt. % in water) solution was diluted with saline to provide a working solution of 6.67 wt. % of polyDADMAC in water. This working solution was used to provide the appropriate amount of flocculant in this study.

Table 4 provides the optimal amount of flocculant for each volume of the 40% blood/saline mixture examined. The optimal amount of flocculant was identified as the amount of flocculant required to provide the fastest rate of red blood sedimentation out of the mixture. The RBCs in each of the mixture volumes examined achieved a visually discernable level of sedimentation in the canister, with a relatively clear fluid being observed above the visually discernable meniscus of settled RBCs at about 15 minutes after the blood/saline mixture had been combined with the flocculant at room temperature. It was observed that the rate of sedimentation varied depending on the amount of flocculant provided in the mixture.

From Table 4, an average of about 0.75 ml to about 1.5 ml of the flocculant working solution (about 50 mg to about 100 mg dry weight polyDADMAC) was optimal for promoting rapid RBC sedimentation in a 100 ml volume of the blood/saline mixture. For a larger 1,200 ml canister having a volume of about 1200 ml, about 9 ml of the polyDADMAC flocculant working solution (or about 600 mg dry weight polyDADMAC) would be provided in the bottom of the canister or on the canister walls to promote rapid RBC sedimentation is a volume of up to 1,200 ml of the blood/saline mixture. In the following studies, about 0.75 ml to about 1.5 ml of the flocculant working solution was used per 100 ml (or 0.75% v/v) of a blood/saline mixture. This concentration value is slightly larger than the 0.4% and 0.6% used in the studies described herein when using the industrial grade flocculant Superflock C-591 version of polyDADMAC.

Based on the identified 0.75% v/v polyDADMAC concentration, a 1,200 ml canister that can collect up to 1,200 ml of a blood-containing fluid will need about 9 ml of the polyDADMAC working solution (or about 600 mg dry weight polyDADMAC).

TABLE 4

| Test blood/saline volume | Optimal Amount of 1/3 diluted 20% polyDADMAC | Need of flocculant per 100 ml of blood saline mixture |
|---|---|---|
| 200 ml of 40% blood | 2-3 ml | 1-1.5 ml |
| 800 ml of 40% blood | 6-8 ml | 0.75~1 ml |
| 1200 ml of 40% blood | 9 ml | 0.75 ml |

Table 4 demonstrates the amount of flocculant that is optimal for achieving sedimentation of RBCs for different volumes of a 40% blood/saline mixture. As shown, 9 ml of the RBC flocculant polyDADMAC (about 600 mg dry weight) provided optimal RBC sedimentation in a volume of 1200 ml of the blood saline mixture.

Example 5

Method of Preparing a Flocculant Treated Canister

The present example describes various methods in which a flocculant may be provided and distributed within and/or on a fluid collection container, particularly a fluid containing blood. While the specific polymeric flocculant, polyDADMAC, is used in the present example, many other polymeric and non-polymeric flocculant may be used in the practice of the present invention for providing the methods and devices described herein.

Vertical Band Coating on Canister Wall. A 1,200 canister was coated with a 9 ml volume of material that contained 600 mg flocculant. The canister was coated in the form of 1" wide vertical band in the canister. This way, only flocculant immersed by the blood/saline mixture is dissolved or released into the mixture to cause RBC sedimentation. In other words, the vertical band of polyDADMAC coating can provide a control release of flocculant proportional to the volume of blood/saline mixture.

Two methods were used to apply the vertical band coating. One is to use a brush to provide a 1" band directly on the canister wall. Another is to apply a flocculant coating on a 1" wide clear tape, and then to adhere the clear tape to the canister wall. The canister has a hydrophobic surface such that it can be difficult for the flocculant solution to stay on the wall. An ozone treatment was developed to change the hydrophobic canister wall to hydrophilic. The flocculant adherence using this technique was improved.

After the coating of the vertical flocculant band, the canister was tested with bovine blood purchased from a commercial vendor. The canister with the flocculant band did facilitate RBC sedimentation. However, the sedimentation rate was somewhat slower. It took more than 20 minutes for the RBC to settle at bottom of the canister. Generally, a faster rate of RBC sedimentation is desired. While not intending to be limited to any theory or specific mechanism of action, the slower rate may be related at least in part to the time needed for the flocculant coating to dissolve and spread throughout the entire blood/saline volume. It takes more time to spread the flocculant from single-band coating to the entire blood/saline mixture. A thinner coating that is distributed throughout the entire canister is expected to accelerate the dissolution and distribution of the flocculant.

Figure 6:
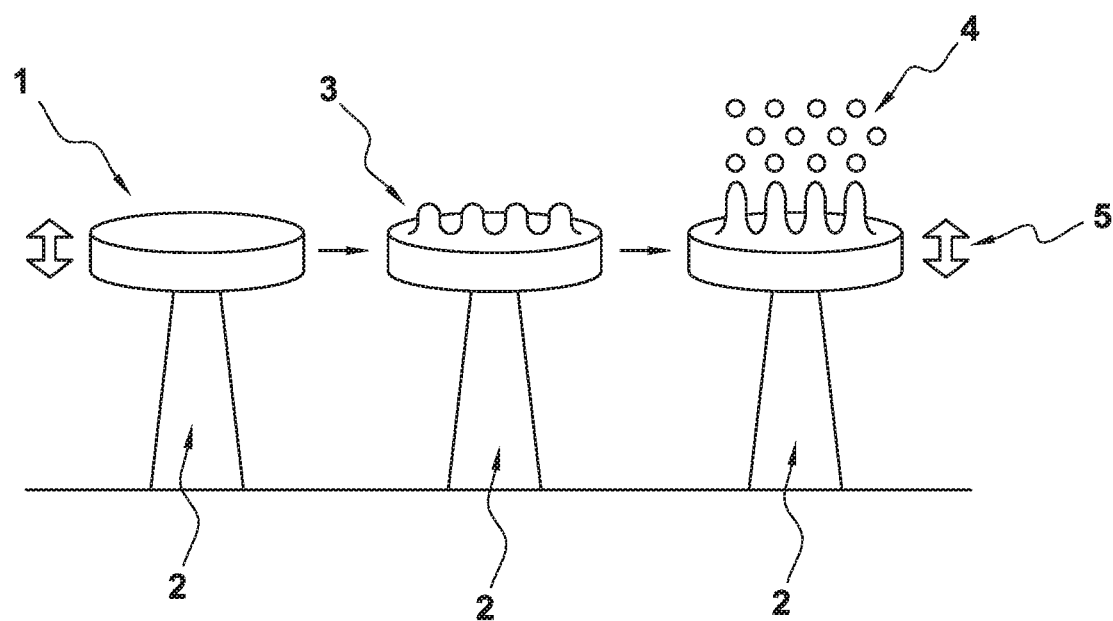
FIG. 6. A flocculant as a particle suspension (4) may be applied to the inside walls of a container by ultrasonic atomization (3, 4, 5) of the flocculant material in a carrier solution. Any conventional ultrasonic atomization device (2) and syringe pump may be used to coat a collection device, such as a 1200 ml canister with a flocculant, for example, polyDADMAC.

Uniform Coating on Entire Canister using the Ultrasound Atomization Technology. An ultrasound based method was used to coat the interior of a blood collection canister. Ultrasound atomization coating is a pressureless, low-velocity (typically on the order of 3-5 inches per second) coating that differentiates itself from spray coating. Piezoelectric transducers convert electrical input into mechanical energy in the form of vibrations. The high frequency sound vibration atomizes liquid into a fine mist spray (FIG. 6). The unpressurized, low-velocity spray significantly reduces the amount of overspray since the drops tend to settle on the substrate, rather than bouncing off it. The mist spray pattern can be controlled and shaped precisely. Spray patterns from as small as 0.070 inches wide to as much as 1-2 feet wide can be generated using these types of specialized spray-shaping equipment. The atomization device used in this process had a 60 kHz ultrasound nozzle.

Figure 7A:
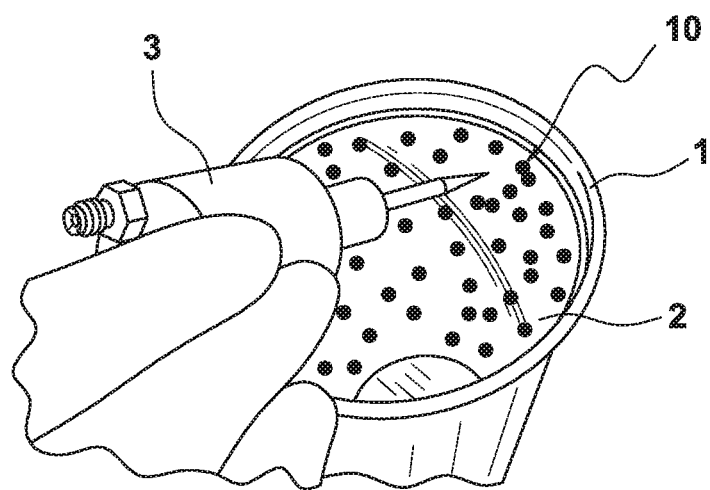
FIG. 7A. Application of a polyDADMAC coating (flocculant particles (10)) onto the surfaces (2) of a collection container (1), such as a 1200 ml canister using an ultrasonic atomization device (3).
Figure 7B:
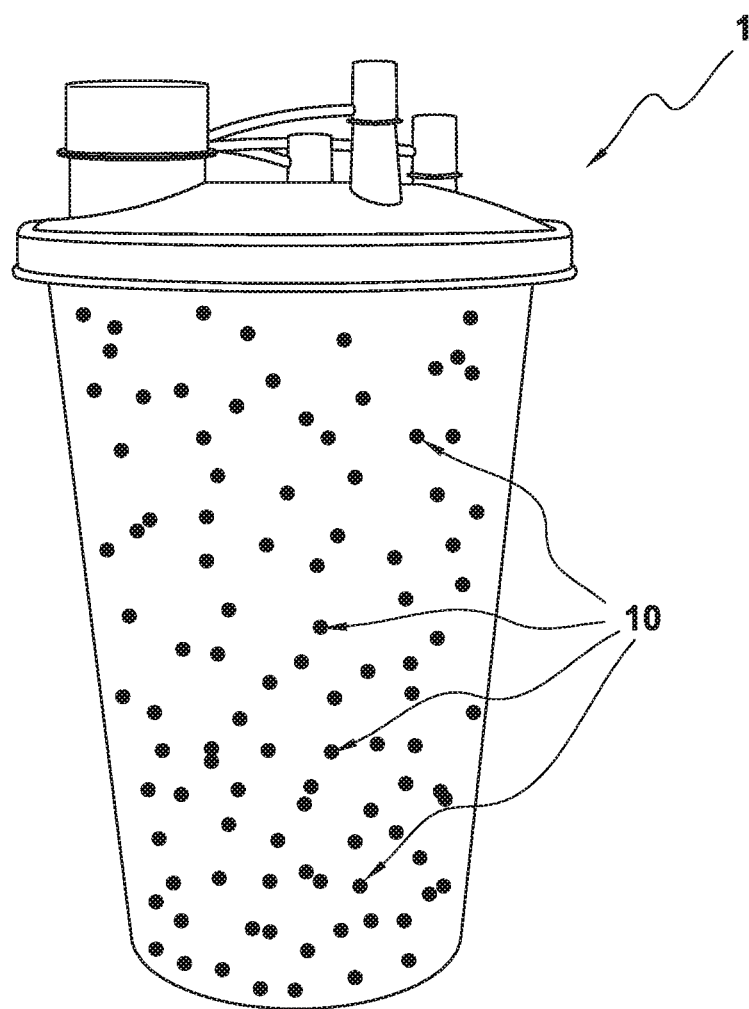
FIG. 7B. The treated 1200 ml canister (1) with two batches of polyDADMAC coating (3) on the surfaces (flocculant particles, 10).

FIG. 7A illustrates the manual coating process of a canister using the ultrasound atomizer. The atomizer tip moves along the canister wall starting from the bottom of the canister gradually moving up to the top of the canister. Regions coated by misty spray turn clear wall to foggy surface, which guides the manual coating process to cover the entire canister wall and to make the coating as uniform as possible based on visual observation. An automatic coating process can be developed in future to make uniform coating.

Multiple parameters were tested, using different concentrations of polyDADMAC, and incorporating high vaporized alcohol, like methanol and ethanol, into the spray solution to accelerate the drying process. The polyDADMAC working solution (prepared in DI (de-ionized) water) provided an optimal misty spray to deposit the flocculant using an ultrasound atomization device at the intensity setting of "10" (FIG. 7A). The syringe pump setting was 60 ml/h. About 4.5 ml of the flocculant coating solution was needed to cover the entire 1,200 ml canister wall. Therefore, to apply 9 ml of the flocculant solution onto the canister, two batches of the flocculant coatings were needed. A 9 ml volume of the flocculant solution contains about 600 mg polyDADMAC.

Between each coating, the canister was allowed to dry completely, either inside an oven for couple of hours or under room temperature for 24 hours. FIG. 7B illustrates a canister applied two batches of coating in its entire wall. Use of a more powerful ultrasound atomization device will permit a greater concentration of the coating solution. In this manner, a single batch of coating may be used to deliver all the polyDADMAC contained in 4.5 ml of the solution, instead of in a 9 ml volume, to provide the flocculant concentration described above.

The flowing protocol provides the manual steps for preparing the flocculant treated (coated) canisters:

Preparation for the Coating

1. Prepare polyDADMAC working solution by mixing one part of 20 wt. % polyDADMAC (Sigma Catalog # 409022) with two parts of DI water.

2. Fill a 60 ml syringe with the polyDADMAC working solution.

3. Set the ultrasound atomization device at the intensity setting of "10".

4. Set the syringe pump rate at 60 ml/hr., and volume deliver of 4.5 ml.

Manual Coating Process

1. Turn on the ultrasound atomization device, start moving the ultrasound nozzle from the bottom of the canister applying misty spray on the wall and bottom of the canister.

2. Gradually moving the ultrasound nozzle from bottom to the top of the canister following the spiral path and ensuring everywhere on the wall is coated with polyDADMAC. The regions coated with the polyDADMAC mist show misty looking as seen in the following picture.

3. Typically, the 4.5 ml diluted polyDADMAC is sufficient to provide one coating to the entire canister.

4. Let the coated canister to dry overnight at the room temperature.

5. After the dry of the first layer of coating, a second layer is applied to the canister in the same way as described above. A total of 9 ml of diluted polyDADMAC will be applied on the canister after two layers of coating.

6. Dry the canister again overnight, then the canister is ready to be used.

Example 6

Estimation of Packing Ratio (η) of the PolyDADMAC Coated 1200 ml Canister

The polyDADMAC coated 1200 ml canister was prepared using a canister having a volume of 1,200 ml, and having the dimensions of a biological waste canister employed in operating rooms. A typical organization of such a canister in an operating room setting is provided in FIG. 5. First, a packing ratio η associated with this coated canister was determined.

Bovine blood purchased from a commercial vendor was used in the present study. This blood had been refrigerated, and then warmed to 23° C. at the time of testing. In addition, the bovine blood contained sodium citrate in order to prevent coagulation.

Bovine blood and saline were added to a flocculant treated canister so as to achieve a defined ratio of blood/saline. To simulate the process in which a liquid containing blood would be provided into a collection canister during a routine operation, for example, a 600 ml volume of a blood/saline mixture (40% blood) was delivered to a flocculant treated canister according to the following technique. A container A was prepared to include 240 ml of blood, and a container B was prepared to contain 360 ml of saline. A serological pipet was used as the aspiration probe. The aspiration probe was connected to an inlet port (the patient port) on the canister via tubing. The canister was further connected to a vacuum line using a second port on the canister, and used to impart a vacuum in the canister. Under vacuum, the pipet was placed in the container including blood or the container including saline to aspirate the respective fluid alternatively into the flocculant containing canister (polyDADMAC) (FIG. 8). A total fluid volume of 600 ml of the 40% blood was therefore provided in the canister.

After all of the blood and saline had been aspirated into the third canister, the mixture was monitored to assess separation/settlement of the RBCs apart from the plasma and saline, in the presence of the flocculant. The volume of the RBC settlement line was recorded every minute for 20 minutes.

The study was conducted using different volumes of the 40% blood/saline mixture solutions (200 ml, 400 ml, 800 ml and 1200 ml). Each study was repeated three times. FIGS. 10A-10D illustrate the change of RBC settlement volume along the time of 20 minutes with the 40% blood mixture. The studies were also performed three times with a 20% blood/saline mixture solution at volumes of 200, 400, 800 and 1200 ml. (FIGS. 9A-9D). In order to obtain an average packing ratio η that would work for different volumes and different blood concentration mixtures in a fluid collected in this canister, two blood concentrations of 20% and 40% , and four different volumes of these, 200 ml to 1200 ml, were examined.

With a 20% blood mixture (20% blood/80% saline), the RBCs settled very quickly in the flocculant treated canister. A visually observable settlement of RBCs of 30 ml ($V_m$) was reached within 10 to 15 minutes at room temperature (FIG. 11A). The average $V_m$ from three repeated experiments and the calculated $V_{ic}$ (based on the measured bovine blood hematocrit (35.4%), and the unknown blood volumes used in the study), of all four different total mixture volumes of the 20% and 40% blood preparations are listed in Table 5.

These experiments demonstrate the polyDADMAC coating facilitated the rapid sedimentation of RBCs out of the blood/saline mixture at room temperature within 15 minutes.

The sedimentation of RBCs in these blood/saline mixtures at room temperature in the absence of a flocculant would have required 3-6 hours.

Estimation of the Packing Ratio η. Using the data from the above experiments, the packing ratio η (see Equation 1) between the settled RBC volume ($V_m$) and the actual RBC volume ($V_c$) can be determined empirically. Table 5 illustrates the empirically determined packing ratio for the 1200 ml Medi-Vac canister, which has the average value of 1.20. Since the packing ratio covers a large range of volumes from 200 to 1200 ml as well as a large range of blood concentrations, the variance of the packing ratio is relatively high, above 13%. These variations in packing ratio also affect the variance in blood volume loss estimation. The following packing ratio η values were calculated for each of the respective blood mixtures. An average value η was then calculated.

TABLE 5

Empirically Determined Packing Ratio:

| Blood Mixtures | Average observed $V_m$ (ml) | Average Vc (ml) | η (Vm/Vc) |
|---|---|---|---|
| 1. 200 ml 20% blood | 18 | 14.58 | 1.23 |
| 2. 400 ml 20% blood | 30 | 29.16 | 1.03 |
| 3. 800 ml 20% blood | 60 | 58.32 | 1.03 |
| 4. 1200 ml 20% blood | 100 | 87.48 | 1.14 |
| 5. 200 ml 40% blood | 30 | 28.01 | 1.07 |
| 6. 400 ml 40% blood | 70 | 56.03 | 1.25 |
| 7. 800 ml 40% blood | 160 | 112.05 | 1.43 |
| 8. 1200 ml 40% blood | 233.3 | 168.08 | 1.39 |
| Average | | | 1.20 |
| Coefficient of Variance | | | 13% |

In this study, the average hematocrit value of bovine blood used was 35.4%, and the derived average packing ratio η was 1.2. Using the formula at Equation 1, the following formula was created to estimate the volume of blood in a fluid collected in the flocculant containing canister:

$$V_b = V_m / 35.4\% \times 1.2 = 2.35 \times V_m$$

The estimate of blood loss for each of the blood mixtures 1-8 are presented in the following Table 6, and compared to the known amount of blood in the sample.

TABLE 6

| Blood Mixtures | $V_m$ (ml) | Estimated blood volume (ml) | Actual blood volume (ml) |
|---|---|---|---|
| 1. 200 ml of 20% blood | 18 | 42.30 | 40 |
| 2. 400 ml of 20% blood | 30 | 70.50 | 80 |
| 3. 800 ml of 20% blood | 60 | 141.0 | 160 |
| 4. 1200 ml of 20% blood | 100 | 235.0 | 240 |
| 5. 200 ml of 40% blood | 30 | 70.5 | 80 |
| 6. 400 ml of 40% blood | 70 | 164.5 | 160 |
| 7. 800 ml of 40% blood | 160 | 376.03 | 320 |
| 8. 1200 ml of 40% blood | 233.3 | 548.3 | 480 |

As demonstrated in the table above, the amount of blood loss calculated using the present formula was correlated with the actual amount of blood in the fluid. The present methods and devices therefore are demonstrated to provide a contemporaneous visual indicator tool of blood volume loss for the physician/health care professional in a surgical setting, which is more accurate than conventional approaches (saline bag use assessment and/or post-surgery estimation from total patient fluid collection).

Based on an observed volume (in ml) of settled RBCs in a graduated canister in the presence of a flocculant, without the requirement of any electrical, temperature, or other material manipulating procedure, a Blood Indicator Panel was devised using the above formula, that provides an immediate visual tool for total blood volume approximation in a collected fluid.

Example 7

Creation of a Blood Volume Indicator Panel for Blood Volume Assessment in a Biological Fluid Receptacle For a user to easily estimate blood volume via a visual inspection of settled RBCs in a receptacle (such as a flocculant containing canister), a blood volume indicator panel with calibrated markings is provided for a fluid collection receptacle, and will indicate a total blood volume approximation in a collected fluid, from the level of settled RBCs in the presence of a flocculant in the collection receptacle. It is envisioned that these collection receptacles may or may not include conventional volumetric measures.

To create the graduated marking for the blood volume indicator panel of the present receptacles (canisters, etc.), the following Equation 2 is used:

$$V_m = V_b \times Hct \times \eta \qquad 2)$$

The Equation 2 will employ an average Hct calculated from a number of animals/human from the same species, and of the same approximate age and gender. For example, for an adult human male, the average Hct is about 45%.

In this study, a blood indicator panel for a large mammal was created using the formula:

$$V_m = 0.43 \times V_b \qquad \text{Equation 3}$$

The formula will use and average Hct in bovine blood of 35.4%, and an average packing ratio η=1.20, as calculated for bovine blood (Table 5).

A 50 ml estimated blood volume mark is provided on the blood volume indicator panel, which corresponds to a visually discernable settled RBC volume of about 21.5 ml. using the Equation 3 (See Table 7). A 100 ml estimated blood volume calibrated mark can be generated on the blood volume indicator panel that corresponds to about the 43.02 ml of the settled RBC volume line of the receptacle, and so forth.

Figure 15:
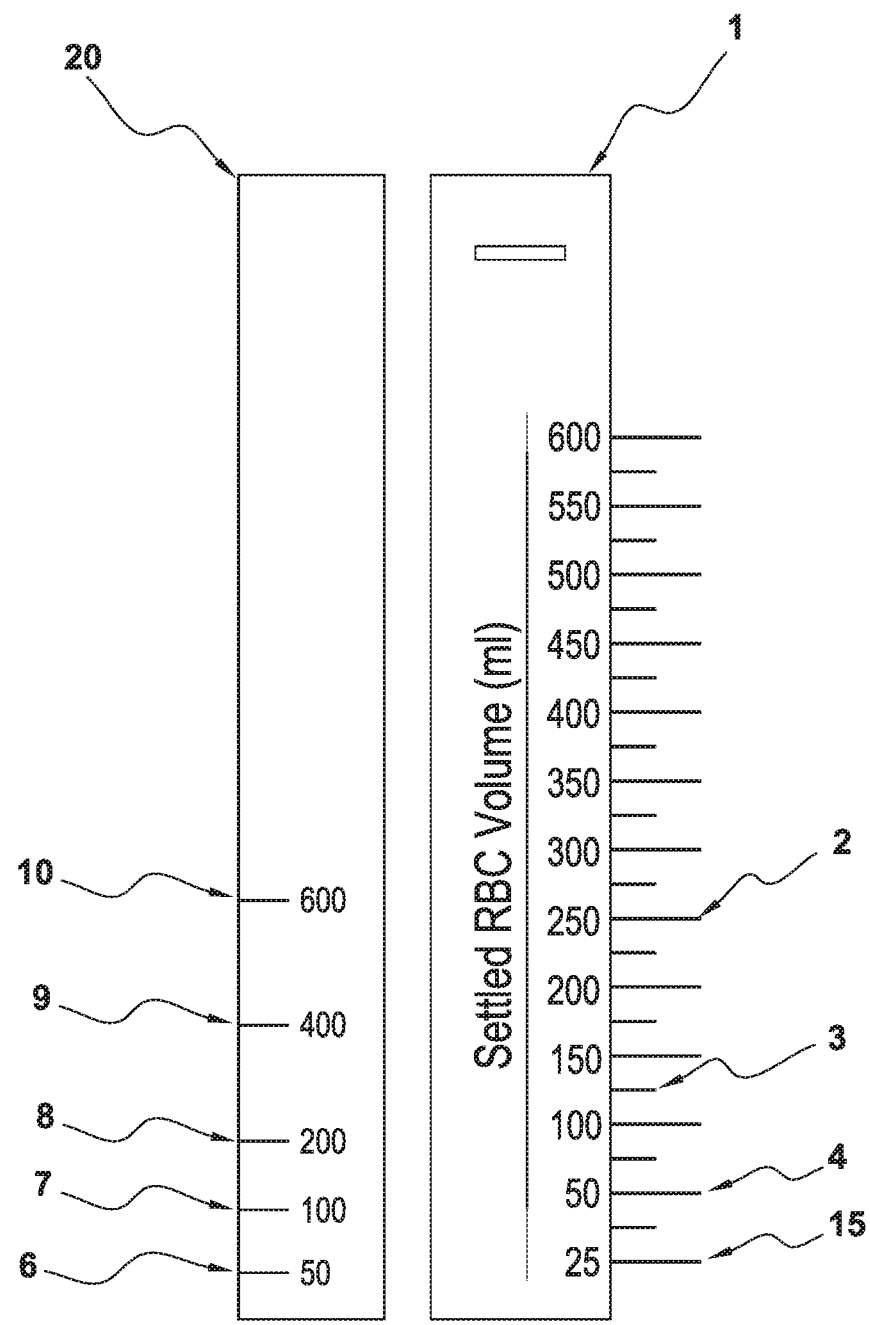
FIG. 15. BIP. A typical BIP suitable for use with a 1200 ml collection container may include a marker for at least the following calibrated approximate blood volumes: 50 ml, 50 ml, 100 ml, 200 ml, 400 ml, and 600 ml. The BIP will provide an accurate approximation of blood volume within a collected fluid containing up to about 50% or less blood. The BIP (20) includes calibrated series of blood volume markings 6 (50 ml), 7 (100 ml), 8 (200 ml), 9 (400 ml), and 10 (600 ml). This BPI is shown alongside a volumetric Settled RBC Volume reference tool (1), that includes conventional volumetric measurements of a collection device 15 (about 25 ml), 4 (about 50 ml), 3 (about 125 ml), and 2 (about 250 ml). The volume of settled RBCs does not provide a direct measure of the volume of blood (indicated on the BIP) in a collected fluid. Instead, the settled RBC level is a reference point from which an appropriate blood volume may be visually identified.

The graduated markings of the blood volume indicator panel provide a series of visually identifiable markings that do not relate to a measure of the volume of material in the canister, but instead to an approximation of the blood volume in the fluid collected in the canister. An illustration of a typical blood indicator panel (BIP), is provided in FIG. 15 (See Left Panel 6, calibrated markings at 50 ml, 100 ml, 200 ml, 400 ml, 600 ml). Inclusion of a Blood Indicator Panel on a conventional collection vessel having standard volumetric markings (See FIG. 16, Right Panel 1), will provide an immediately visual estimation of blood volume in a collected fluid, without the necessity of performing mathematical calculations or other manipulations of collected or sedimented materials. As shown, the blood volumes identified with the calibrated markings of the BPI do not coincide with the conventional volume of settled RBCs in the fluid. Instead, the volume of settled RBCs is used as part of a calculation together with hematocrit and the defined aspect ratio to provide an approximation of blood volume. In the absence of a flocculant, the volume of blood in a liquid would not be possible to approximate within less than about 3-6 hours because, among other things, RBCs do not begin to settle until well after 3-6 hours. In addition, the presence of flocculant, alone, while facilitating rapid RBC sedimentation, does not immediately approximate the amount of blood in a liquid. As demonstrated in the present results, the volume of settled RBCs in a liquid was less than about 50% of the actual blood volume known to be contained in a test fluid containing a known amount of blood. The volume of settled RBCs in the presence of flocculant has to be further corrected to accommodate blood average hematocrit and packing ratio, to provide an approximate blood volume in a liquid.

Figure 8:
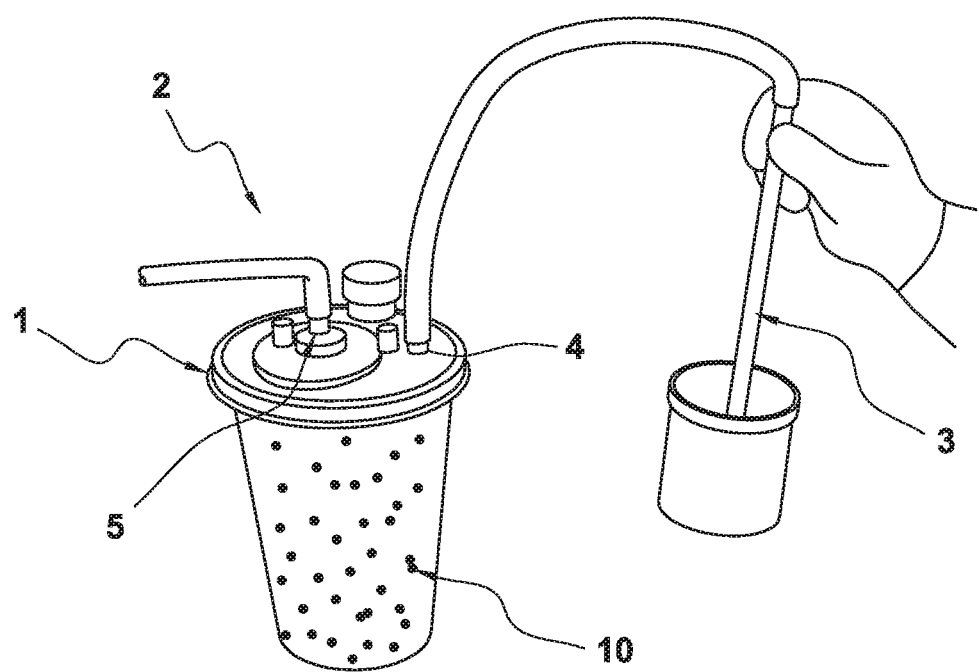
FIG. 8. Flocculant (10) treated canister having a cap (1), the cap (1) having a first inlet port (4) connecting the canister by a length of tubing (4) to a container having a volume of a blood mixture, and a second vacuum port (5) that connects the canister through a length of tubing to a vacuum source, so as to create a suction force within the canister.
Figure 9A:
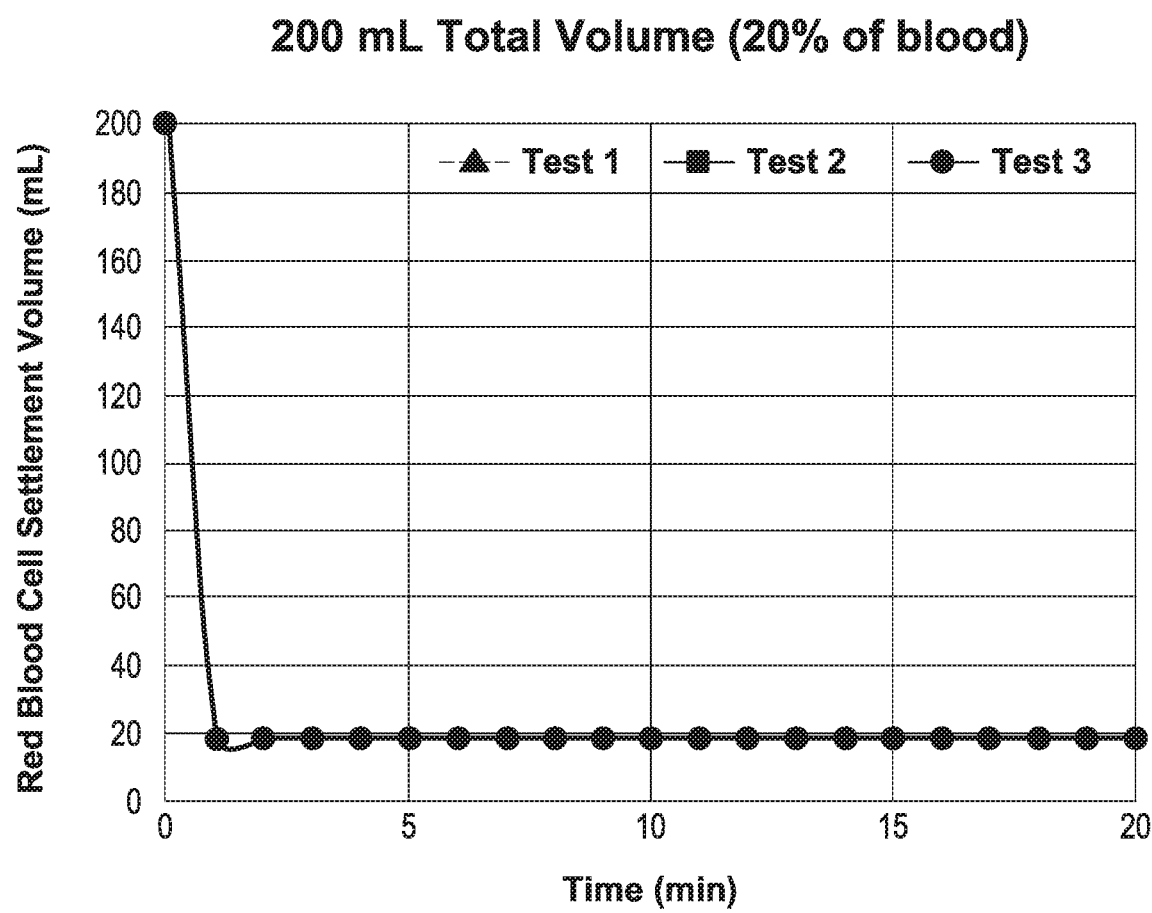
FIG. 9A-9D. The change of RBC settlement volume along the 20-minute time in the case of 20% blood/saline mixture experiment. The total blood/saline mixture volumes are 200 ml (FIG. 9A), 400 ml (FIG. 9B), 800 ml (FIG. 9C), and 1200 ml (FIG. 9D), respectively. Markers were created as part of a BIP to provide an approximation of blood volume (not settled RBC volume).
Figure 9B:
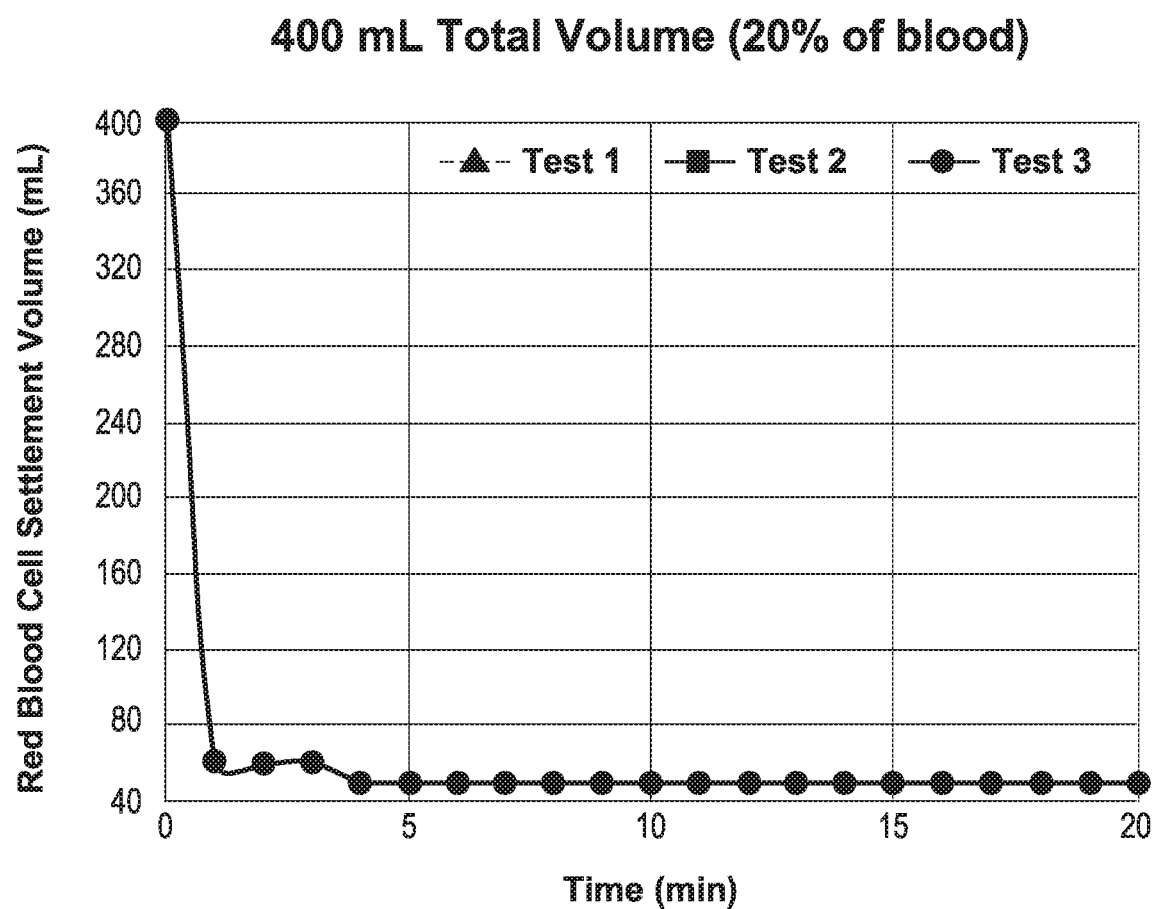
Figure 9C:
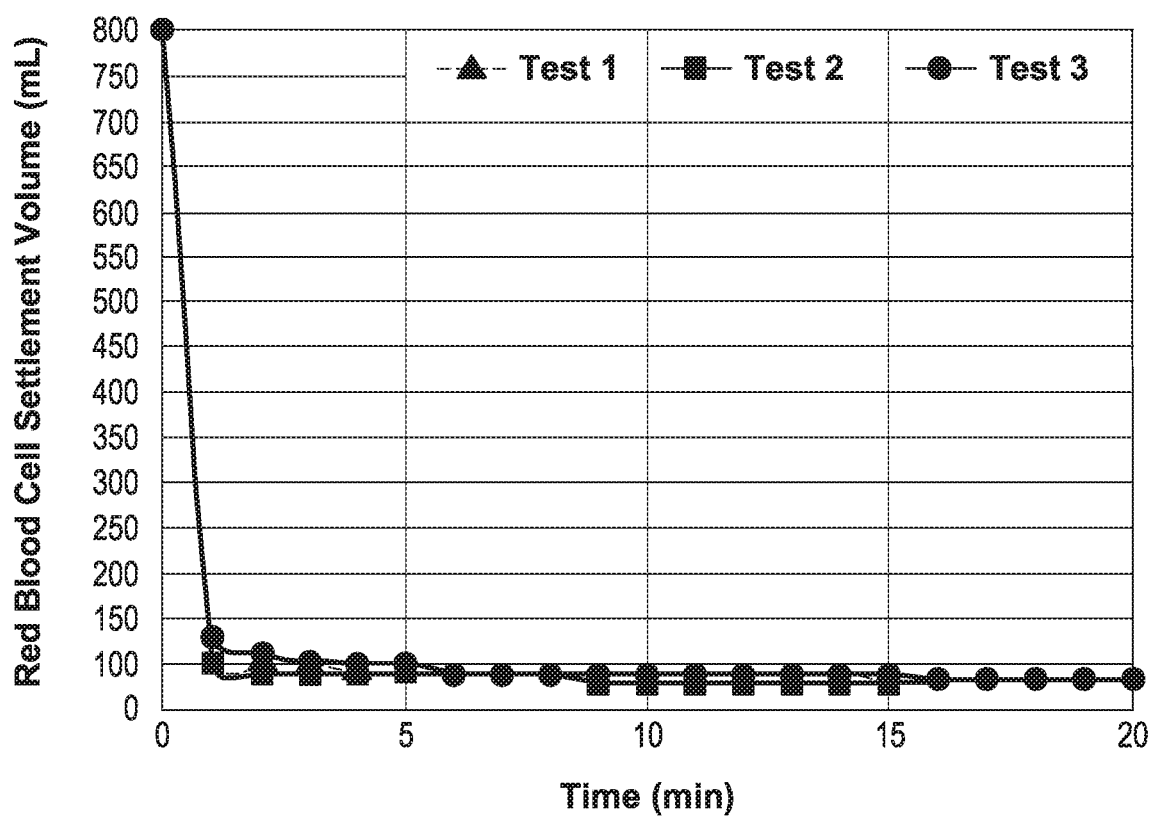
Figure 9D:
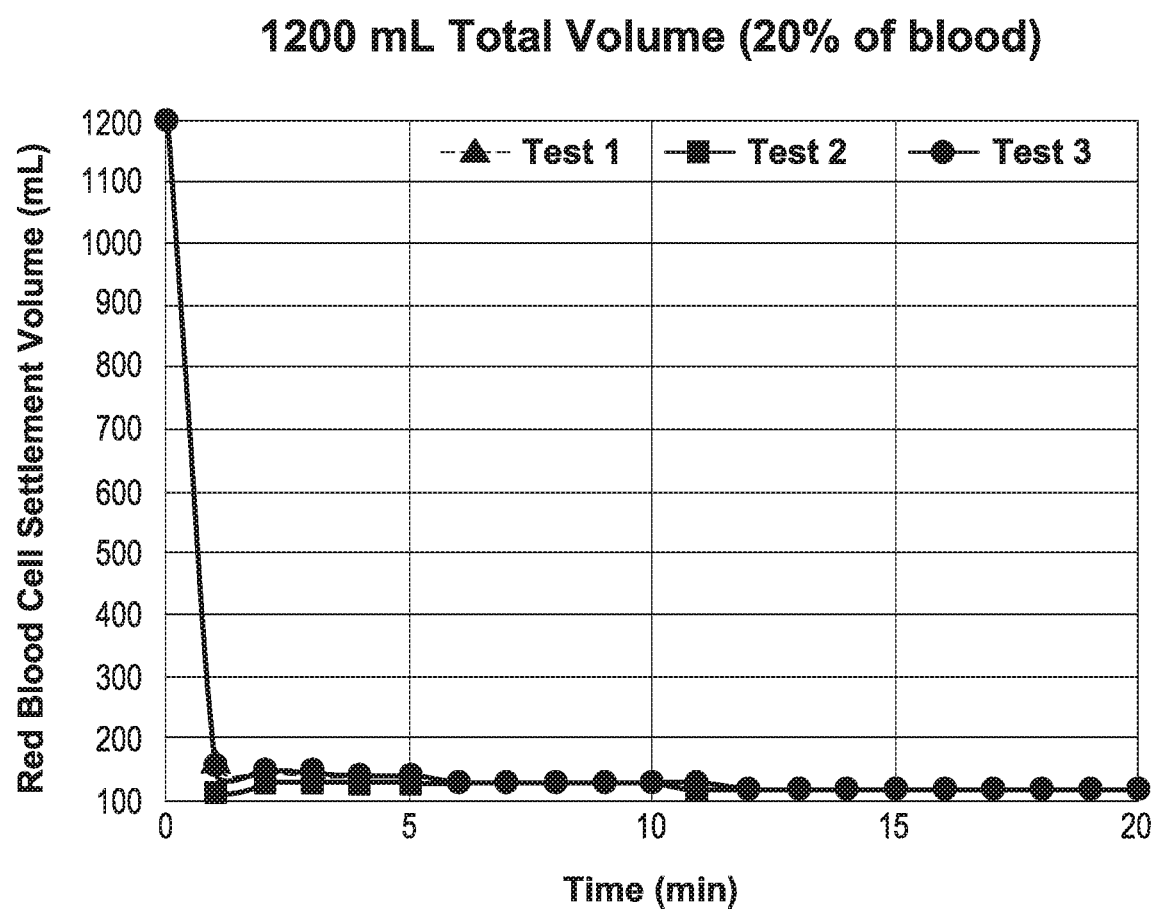

The BIP Panel is created based on the derivation of an average hematocrit (Hct), for example, the average Hct for human, bovine, equine, etc. To correct for Hct differences in individual patients/animals, such as differences in individual Hct due to gender, species, age, etc., the approximate blood volume value indicated on the BIP may be adjusted by a factor that corrects for significantly higher or lower individual hematocrit values. For example, if the measured Hct value from a patient is lower, for example, 80% of the typical Hct of an adult human male, then the blood volume indicator value on the panel observed for that patient will be divided by 80%, so as to provide an even closer approximation of the estimated blood volume in the receptacle. More particularly, if the blood volume indicator value on the panel is 50 ml according to the graduated markings on the indicator panel, the actual blood volume in the biological material collected from this patient would be calculated to be 62.5 ml where the patient's Hct is 80% of the typical Hct value. Similarly, if the measured Hct value of a patient is higher, for example 110% of a typical adult male hematocrit value, then the blood volume indicator value on the blood volume indicator panel would be divided by 110%, which will yield a lower blood volume. For example, if the blood volume indicator value on the blood volume indicator panel is 100 ml, then the actual blood volume loss for the patient would be calculated to be 90.9 ml, so as to correct for the patient's higher than average Hct. (e.g., 10% higher). FIG. 8 illustrates a 1200 ml canister with a blood volume indicator panel.

Figure 12:
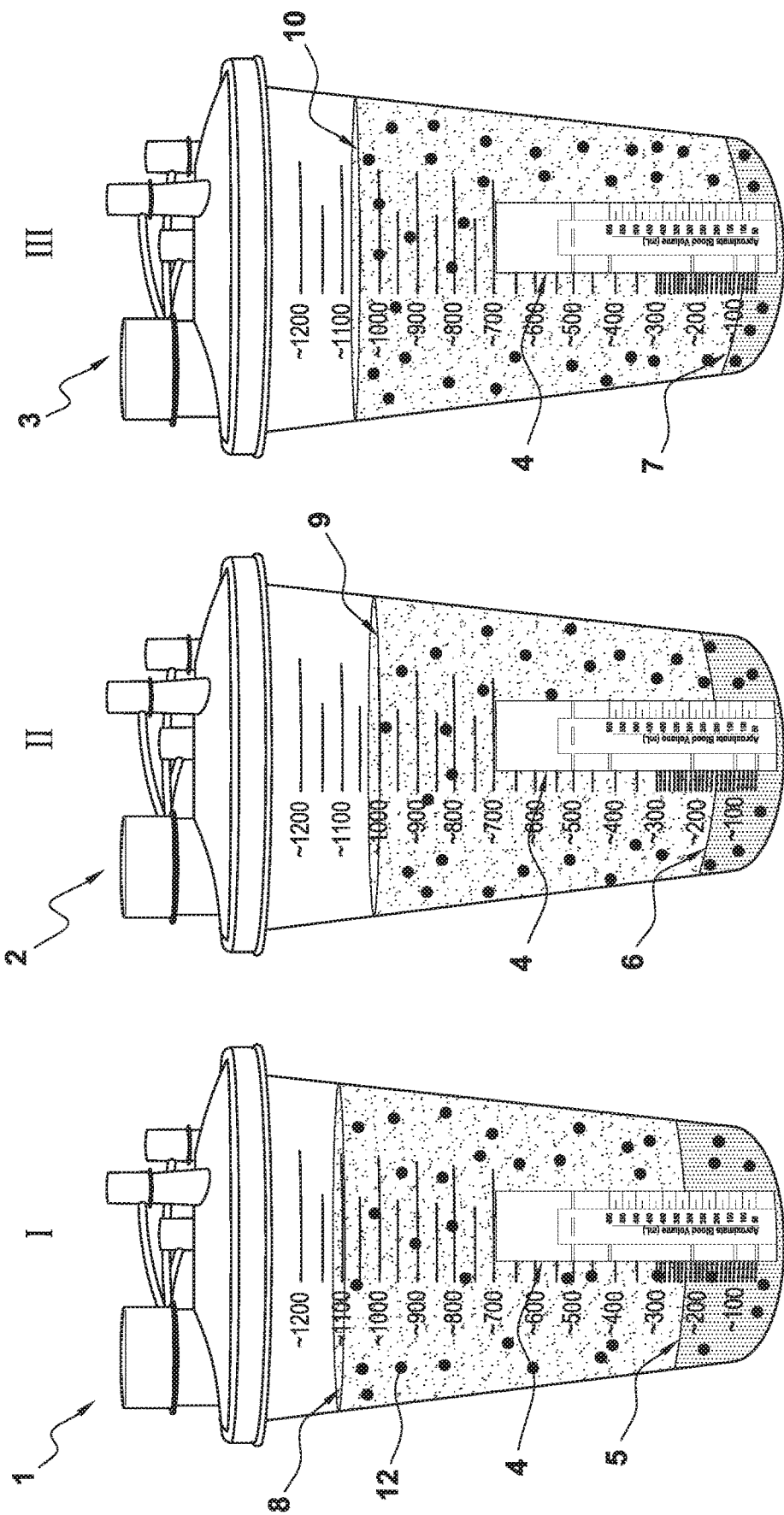
FIG. 12. Three flocculant-treated canisters (left to right, labeled as I, II, and III), were prepared to include a Blood Indicator Panel (4). As illustrated, the Blood Indicator Panel (4) is presented as a separate indicator panel, and may be provided alongside conventional volumetric markings on the canister. The Blood Indicator Panel includes a series of calibrated markings that provide an approximation of blood volume. The blood/saline mixtures examined in each canister were 50% blood (I), 30% blood (II) and 20% (III). The BIP (see vertical white bar), at canister 12III shows a settled RBC level of about 50 ml in the presence of a flocculant (flocculant particles, 12), which corresponded to a calibrated BIP reading of about 116 ml.

The particular Blood Indicator Panel as placed on a collection canister is shown in FIG. 12. The BIP was created to provide a blood volume estimation in a volume of a 20% blood/saline mixture or in a 40% blood/saline mixture using bovine blood. The Blood Indicator Panel may also be useful for assessing the volume of human blood in a liquid sample. This is because both bovines and humans are mammals, and blood from bovines and humans share many characteristics, including similar average hematocrit.

Example of the Blood Indicator Panel markings to be used on a 1200 ml canister. These calibrated blood volume markings correspond to an estimate of the volume of blood contained in a fluid sample, compared in the table to the corresponding sedimented RBC volume (indicated by the value $V_m$ in the table). (Bovine blood with sodium citrate)

TABLE 7

| Calibrated Approximation of Blood Volume ($V_b$) BIP | Graduated Volume Marking of Sedimented RBCs ($V_m$) (about 20% blood to 50% Blood containing Fluids) |
| --- | --- |
| 50 ml | 21.5 ml |
| 100 ml | 43.0 ml |

TABLE 7-continued

| Calibrated Approximation of Blood Volume ($V_b$) BIP | Graduated Volume Marking of Sedimented RBCs ($V_m$) (about 20% blood to 50% Blood containing Fluids) |
| --- | --- |
| 200 ml | 86.0 ml |
| 400 ml | 172.0 ml |
| 600 ml | 258.0 ml |

This study successfully developed the prototype for a BIP using a RBC flocculant, polyDADMAC coated biological fluid collection canister (1200-ml). This size canister is used in operating rooms for human patients, adult and pediatric. The evaluation of the prototype using bovine blood has shown a quick sedimentation of RBCs in the presence of this exemplary RBC flocculant, and the achievement of stable RBC sedimentations within 20 minutes. Calibrated markings on the specially designed BIP were designed for this collection canister, and may be used to provide a visual estimation of total blood volume in a collected mammalian liquid. If the patient's measured hematocrit is different from the typical hematocrit used to create the calibrated BIP markings, the calibrated blood volume can be corrected to accommodate the percent blood hematocrit to the individual blood volume amount.

The following provides the average hematocrit for an adult man and for an adult woman: Normal Hct Values: Men—42-52% (Average Hct, 47); Women—37-47% (Average Hct, 42).

Example 8

Creation of 100 ml Canister with Flocculant

A 100 ml canister was prepared, to contain about 50 mg flocculant. In this example, the RBC flocculant used was polyDADMAC. The flocculant was provided in a volume of the polyDADMAC working solution described herein.

In a typical operating room setting, smaller volumes of fluid containing blood and other materials (tissue, urine, non-blood fluid, etc.) will be aspirated from a surgical field. The aspiration of these fluids results in an undetermined loss of blood from the patient. A smaller container may be prepared according to the present invention to accommodate the estimation of blood loss in these small, sometimes critical, volumes of collected fluid. Therefore, these 100 ml receptacles containing a RBC flocculant, such as polyDADMAC, are provided and are especially useful for determining blood volume in small amounts of collected fluid. These devices may be used, for example, in pediatric applications (infant) as well as in low volume critical fluid collection procedures.

The aspect ratio of the 100 ml collection device was calculated to be 0.96. The small 100 ml container with the RBC flocculant was used in the study described in Example 9.

Example 9

Fresh Blood Loss Estimation

The present example is provided to demonstrate the utility of the methods and devices for use for estimating blood loss in a fluid containing mammalian fresh blood (no anti-coagulants). In this example, a non-blood material present in the fluid was saline. The present example examines a technique for estimating blood loss using fresh, never refrigerated, volume of mammalian blood. Further, the blood did not contain calcium citrate, or any other anti-coagulants. In the present study, the fresh blood specimen was obtained from an adult horse. Thus, the devices and methods are especially useful in the approximation of blood loss in mammals, including humans and veterinary animals (horses, dogs, cats, cows, bulls, sheep, pigs, etc.).

In this example, blood was collected from a live, adult horse (approximately 12 years old, weight 1,200 pounds), having no known clinical pathologies, and not on any known medications. The animal was being treated for a lame foot, and was being given a nerve block to manage pain. Unlike blood collected from a commercial vendor, which contains an anticoagulant such as sodium citrate (used in the prior examples), no anticoagulants or other drugs were present in the blood collected from the horse used in this study.

A total of twelve (12) canisters having a total volume capacity of 100 ml were used in the present study. The canisters were marked with demarcations along the side of the canisters at 50 ml and 100 ml increments. The aspect/ratio of the 100 ml container, D:H (Diameter vs. Height) was calculated to be about 0.96. Comparatively, the aspect ratio of the 1200 ml canister is about 0.61. Typically, the larger the aspect ratio of the collection device, the more quickly RBCs contained within any blood in the collected liquid will settle out in the collection device. Therefore, the rate of RBC sedimentation in the 100 ml collection device was expected to be more rapid compared to the sedimentation rate of RBCs in a 1200 ml canister, in the presence of the RBC flocculant, under similar conditions.

The 100 ml dry canisters received 50 mg of the RBC flocculant, polyDADMAC, research grade (Sigma Catalog #409022). (See Example 7). Other RBC flocculants, as well as industrial grade versions of these flocculants, including PEI, PAM and others, may be expected to be useful in the present methods and devices.

Figure 18:
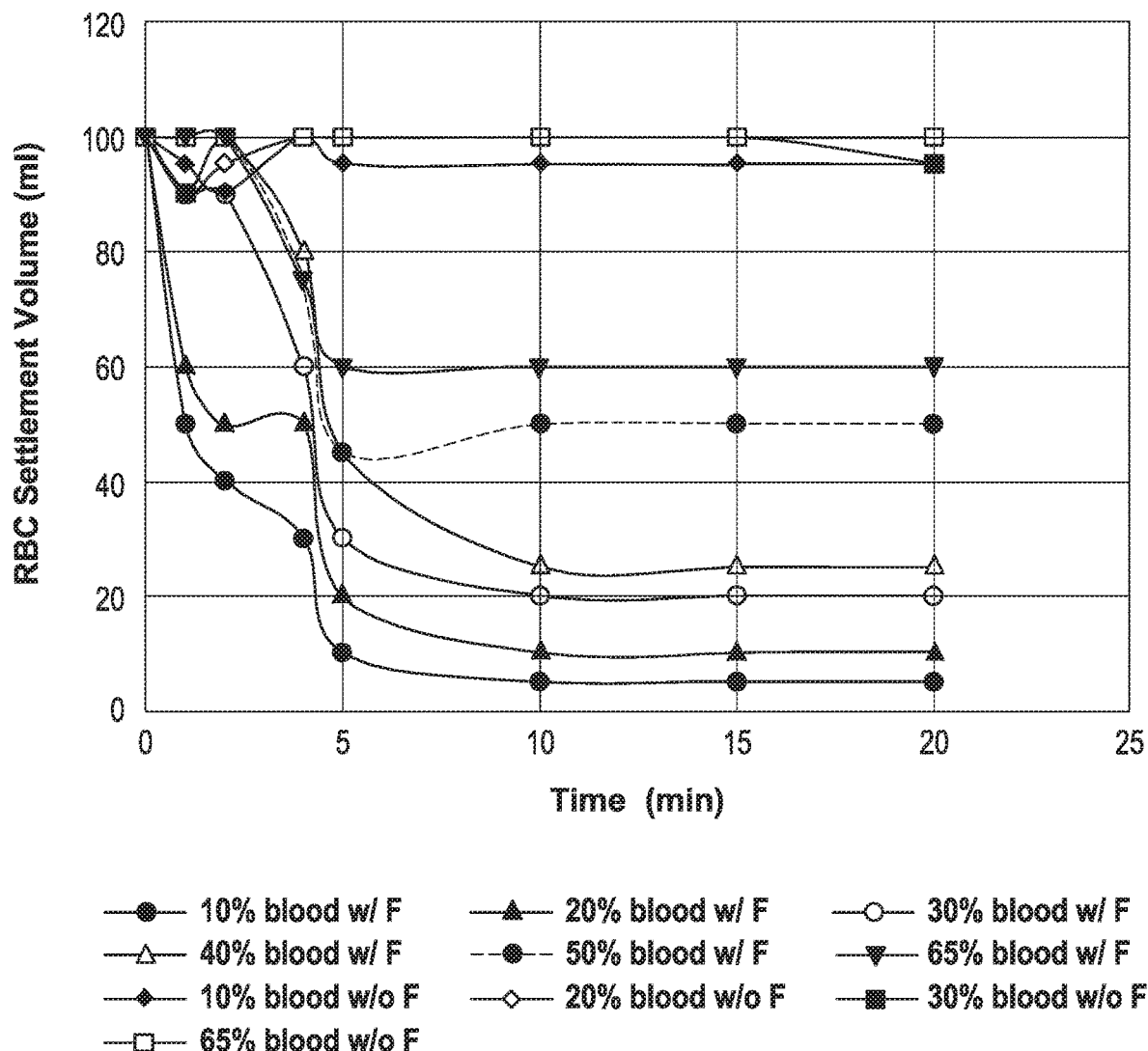
FIG. 18. Equine Blood Study: Comparison of RBC sedimentation in 100 ml container with or without flocculant (volumetric readings approximated from visual inspection using course volumetric markings on containers. RBC sedimentation in 100 ml container with flocculant. 10% blood with flocculant (w/F); 20% blood with flocculant (w/F); 30% blood with flocculant (w/F); 40% blood with flocculant (w/F); 50% blood with flocculant (w/F); 65% blood with flocculant (w/F); No visually detectable sedimentation of RBCs was observed in the 10% blood without flocculant (w/o F); 20% blood without flocculant (w/o F), 30% blood without flocculant (w/o F); 40% blood without flocculant (w/o F) (not shown); 50% blood without flocculant (w/o F, not shown); or 65% blood without flocculant (w/o F) mixtures examined at room temperature over the test period (0 to 25 minutes).
Figure 19:
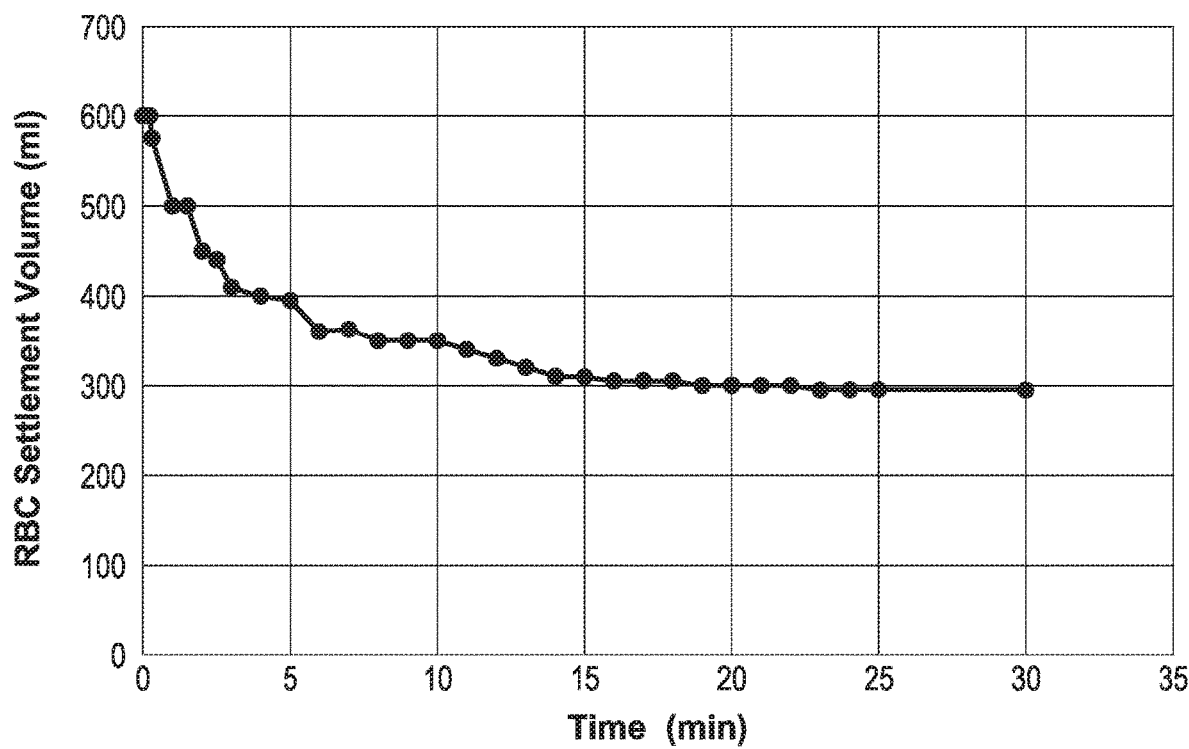
FIG. 19—Equine Fresh Blood Study: RBC sedimentation from a 61.6% blood/saline mixture in a flocculant coated 1200 ml canister. About 400 ml of fresh equine blood was combined with 250 ml saline. The volume of RBC sedimentation was recorded. The RBCs began to settle out within 1 minute (500 ml RBC sedimentation volume). The RBCs settled to a volume of about 300 ml by 15 minutes, and remained stable at this sedimentation volume until the end of the observation period.

The amounts of fresh equine blood and saline indicated in Table 8 were then added to each of the canisters, and RBC sedimentation volume was recorded every minute for 20 minutes:

Blood from an adult horse was drawn, and a volume of the fresh blood at body temperature was added to each of the canisters in the amounts indicated above. The top on each of the canisters was then put in place, the contents mixed so as to assure proper mixture of saline, blood and flocculant. Each canister was allowed to sit undisturbed at room temperature, and observed. The time at which sedimentation of RBCS was observed was recorded at 1 minute intervals up to 30 minutes. FIG. 18 presents the RBC sedimentation rates of the various mixtures. Essentially no visually detectable RBC sedimentation was observed with the blood mixtures in the absence of flocculant. In contrast, RBC sedimentation was rapidly observed in all blood mixtures containing flocculant within 5 minutes at room temperature.

Table 9 presents the hematocrit of various large animals. The values for mean corpuscular hemoglobil (MCH), mean corpuscular hemoglobin concentration (MCHC), mean corpuscular volume (MCV), and packed cell volume (PCV), and may be employed in providing an appropriate customized Blood Indicator Panel and blood volume approximation method as described in the present disclosure.

TABLE 9

Normal Values for Erythron Data in Ruminants and the Horse

|  | Cattle | Sheep | Goats | Horses |
|---|---|---|---|---|
| PCV (%) | 24-46 | 27-45 | 22-38 | 32-53 |
| Erythrocytes (×10$^6$/L) | 5-10 | 9-15 | 8-18 | 6.7-12.9 |
| Hemoglobin (g/dl) | 8-15 | 9-15 | 8-12 | 11-19 |
| MCV (fl) | 40-60 | 28-40 | 16-25 | 37-58.5 |
| MCH (pg) | 11-17 | 8-12 | 5.2-8 | 12.3-19.7 |
| MCHC* (g/d1) | 30-36 | 31-34 | 30-36 | 31-38.6 |
| Reticulocytes | 0 | <0.5% | 0 | 0 |
| Erythrocyte diameter (m) | 4-8 | 3.2-6 | 2.5-3.9 | 5-6 |
| Erythrocyte fragility (percent NaCl) |  |  |  |  |
| Minimum (beginning hemolysis) | 0.52-0.66 | 0.58-0.76 | 0.74 | 0.54 |
| Maximum (complete hemolysis) | 0.44-0.52 | 0.40-0.55 | 0.44 | 0.34 |

TABLE 8

Fresh Equine Blood Study: Rate of Sedimentation of RBC

| With | | RBC Sedimentation/ml ($V_m$) | | | | | | |
|---|---|---|---|---|---|---|---|---|
| Flocculant | Blood/Saline | 1 min | 2 min | 4 min | 5 min | 10 min | 15 min | 20 min |
| 1. 10% Blood | 10 ml/90 ml | 50 | 40 | 30 | 10 ml | 10 ml | 10 ml | 10 ml |
| 2. 20% Blood | 20 ml/80 ml | 60 | 50 | 50 | 20 | 20 | 20 | 20 |
| 3. 30% Blood | 30 ml/70 ml | 90 | 90 | 60 | 30 | 30 | 30 | 30 |
| 4. 40% Blood | 40 ml/60 ml | 100 | 100 | 80 | 45 | 45 | 30 | 40 |
| 5. 50% Blood | 50 ml/50 ml | 100 | 100 | 75 | 45 | 45 | 45 | 45 |
| 6. 65% Blood | 65 ml/35 ml | 100 | 100 | 75 | 60 | 65 | 65 | 60 |

| Controls: Without Flocculant | Blood/Saline | 1 min | 2 min | 4 min | 5 min | 10 min | 15 min | 20 min |
|---|---|---|---|---|---|---|---|---|
| 7. 10% Blood | 10 ml/90 ml | ND | ND | ND | ND | ND | ND | ND |
| 8. 20% Blood | 20 ml/80 ml | ND | ND | ND | ND | ND | ND | ND |
| 9. 30% Blood | 30 ml/70 ml | ND | ND | ND | ND | ND | ND | ND |
| 10. 40% Blood | 40 ml/60 ml | ND | ND | ND | ND | ND | ND | ND |
| 11. 50% Blood | 50 ml/50 ml | ND | ND | ND | ND | ND | ND | ND |
| 12. 65% Blood | 65 ml/35 ml | ND | ND | ND | ND | ND | ND | ND |

* ND = Non-detectable by visual inspection.

TABLE 9-continued

Normal Values for Erythron Data in Ruminants and the Horse

| | Cattle | Sheep | Goats | Horses |
|---|---|---|---|---|
| Erythrocyte sedimentation rate (mm/1 hour) | 0 | 1-2.5 | 0 | 50-60 |
| Erythrocyte life span (days) | 160 | 140-150 | 125 | 140-150 |

(MCH, Mean corpuscular hemoglobin; MCHC, mean corpuscular hemoglobin concentration; MCV, mean corpuscular volume; PCV, packed cell volume.)

TABLE 10

Normal Values for Leukogram Data (Adult Aminals)

| Biological Component | Cattle | Sheep | Goats | Horses |
|---|---|---|---|---|
| White blood cells ($\times 10^3/\mu l$) | 4-12 | 4-12 | 4-13 | 5.4-14.3 |
| Neutrophils ($\times 1.0^3/\mu l$) | 0.6-4 | 0.7-6 | 1.2-7.2 | 2.3-8.6 |
| Bands ($\times 10^3/\mu l$) | 0-0.12 | Rare | Rare | 0-1 |
| Lymphocytes ($\times 10^3/\mu l$) | 2.5-7.5 | 2-9 | 2-9 | 1.5-7.7 |
| Monocytes ($\times 10^3/\mu l$) | 0.025-0.84 | 0-0.75 | 0-0.55 | 0-1 |
| Eosinophils ($\times 10^3/\mu l$) | 0-2.4 | 0-1 | 0.05-0.65 | 0-1 |
| Basophils ($\times 10^3/\mu l$) | 0-0.2 | 0-0.3 | 0-0.12 | 0-0.29 |
| Neutrophil/lymphocyte (N:L) ratio | 0.3-0.6 | 0.3-0.7 | 0.6-3.6 | 0.8-2.8 |

TABLE 11

Normal Values for Hemostatic Data in Ruminants and the Horse

| Blood Component | Cattle | Sheep | Goats | Horses |
|---|---|---|---|---|
| Platelet count ($\times 10^{-3}$/L) | 100-800 | 250-750 | 300-600 | 100-600 |
| Fibrinogen (mg/dl) | 200-500 | 100-500 | 100-400 | 200-400 |
| Prothrombin time(s) | 22-55 | —* | 9.5-12.5 | 7-9 |
| Activated partial thromboplastin time(s) | 44-64 | — | 28-52 | 37-54 |
| Fibrin/fibrinogen degradation products (µg/ml) | <8 | <8 | — | <32 |

(Modified from Duncan J R et al: Veterinary laboratory medicine, Ed 2, Ames, Iowa, 1986, Iowa State University Press; and Kaneko J J: Clinical biochemistry of domestic animals, Ed 3, New York, 1980.)

Example 10

Blood Volume Estimation in a Fluid using a Canister with Fresh Equine Blood (no anti-coagulant) in the presence of a Flocculant The present example was performed with fresh blood drawn from an adult horse (12 years old, about 1,200 pounds). The horse blood did not contain any anticoagulant. The hematocrit of horse blood is between 32% and 53%. The horse blood was used immediately after having been drawn, and was at body temperature (about 101° F., 38.3° C.) at the time it was combined with saline in the presence of flocculant, polyDADMAC (600 mg).

A 1,200 ml canister that had been coated by spray application of about 9 mls of polyDADMAC working solution as the flocculant was used. Thus, the 1,200 ml canister was coated evenly with a total of about 600 mg dry weight polyDADMAC as the flocculant. Because the flocculant was evenly distributed along the walls of the canister, the amount of flocculant is released in proportion to the volume of fluid provided in the treated canister.

The following volumes of settled RBCs were recorded over time.

A volume of 400 ml fresh horse blood (not refrigerated, body temperature, no anti-coagulants), was placed in the treated canister. A known volume of 250 ml saline was added to the canister. The total volume was 650 ml of fluid in the canister. This provided a 61.5% blood solution. The volume of settled RBCs (gravity only, no centrifugation), $V_m$, was recorded immediately upon mixing, up to a period of 30 minutes.

After being allowed to settle undisturbed for 30 minutes, the canister was manually agitated, and then allowed to sit at room temperature again. The agitated blood containing canister was again observed for evidence of settlement of RBCs at room temperature.

TABLE 12

| Time (min) | RBC (settled RBC) |
|---|---|
| 0 sec | 600 ml |
| 20 sec | 600 ml |
| 30 sec | 575 ml |
| 1 min | 500 ml |
| 1.5 min | 500 ml |
| 2.0 min | 450 ml |
| 2.5 min | 440 ml |
| 3.0 min | 410 ml |
| 4.0 min | 400 ml |
| 5 min | 395 ml |
| 6 min | 360 ml |
| 7 min | 360 ml |
| 8 min | 350 ml |
| 9 min | 350 ml |
| 10 min | 350 ml |
| 11 min | 340 ml |
| 12 min | 330 ml |
| 13 min | 320 ml |
| 14 min | 310 ml |
| 15 min | 310 ml |
| 16 min | 305 ml |
| 17 min | 305 ml |
| 18 min | 305 ml |
| 19 min | 300 ml |
| 20 min | 300 ml |
| 21 min | 300 ml |
| 22 min | 300 ml |
| 23 min | 295 ml |
| 24 min | 295 ml |
| 25 min | 295 ml |
| 30 min | 295 ml |

At the end of the 30 minute observation period, the canister was manually shaken, and allowed to sit. The re-sedimentation of RBCs occurred, and was observed every minute for 30 minutes, and resulted in the observation of settled RBC levels as indicated in Table 14.

TABLE 14

| Time | RBC (settled RBC) |
|---|---|
| 0 | 0 ml |
| 1 min | 0 ml |
| 2.5 | 0 ml |
| 3.0 min | 350 ml |
| 4.0 min | 300 ml |
| 5.0 min | 300 ml |
| 8 min | 300 ml |
| 10 | 300 ml |
| 20 | 300 ml |
| 30 | 300 ml |
| 40 | 300 ml |
| 50 min | 250 ml |

From this study it is demonstrated that the settled volume of RBC's in a solution containing whole fresh blood remains relatively stable up to about 30-40 minutes at room temperature. With agitation, it appears that RBCs in the fresh blood sample again settled to provide a discernable RBC sedimentation volumetric line, $V_m$, very quickly (3 to 4 minutes verses 16-19 minutes, settled RBC volume about 250 ml to 300 ml.). The actual known volume of fresh blood present in the fluid was 400 ml.

The total approximation of blood volume may be calculated by the formula using the average hematocrit of the type of animal (42.5%, horse average Hct), the Vm (observable settled RBC volume in ml), and a new packed ratio value (n) determined for horse blood via experimentation with multiple equine blood sample assessments of settled RBC volume ($V_m$) and Hct information, a visual Blood Indicator Panel may be created and provided along the vertical axis of a collection canister for use with large animals, such as horses. This would provide an immediately visually discernable approximation of blood volume in a biological fluid containing horse blood. The development of a Blood Indicator Panel for a treated canister or other receptacle may be used to provide a visual indicator of equine blood volume loss, and especially for assessing a more exact equine blood loss, than is presently available. An equine Blood Indicator Panel may be developed employing the information and results presented here, by one of ordinary skill in the veterinary arts, without more than ordinary and routine experimental optimization trial and error.

Example 11

Human Pediatric Applications for Use in Estimating Blood Loss

The present example is provided to provide canisters and methods for efficient measurement of blood loss in a pediatric patient. As used in the present example, a pediatric patient is defined as an individual up to 12 years of age having a body weight of up to 70 to 80 pounds.

A person's total blood volume (TBV) is related to body weight. The TBV of a child is around 75-80 ml/kg and is higher in the neonatal period (from 85 ml/kg it rises to a peak of 105 ml/kg by the end of the first month and then drops progressively over ensuing months). Thus, the TBV of a 3.5-kg 2-week-old will be about 350 ml while that of a 10-kg 15-month-old will be about 800 ml.

Because of the much reduced total volume of blood in a pediatric patient, it is especially important to provide a blood collection and blood loss estimation system and device that are designed for estimating blood loss accurately from a smaller volume of blood collected from a pediatric patient. The specifically designed pediatric blood loss estimation devices of the present invention are therefore crafted with a container having the herein described flocculant and canister demarcations with a total volume capacity of less than 1000 ml, such as about 500 ml or even about 250 ml, in the case of an infant or neonate.

A large acute loss of blood volume in a pediatric patient may compromise the circulation, and therefore blood loss should be carefully monitored so as to be able to detect a volume of blood loss of about 12% of the TBV (around 10 ml/kg) of the specific pediatric patient, assuming the child is in a stable condition and has a normal blood hemoglobin (Hb) level at the beginning of a procedure.

By way of example, a suitable pediatric blood loss collection device would, in some embodiments, have a capacity of 250 mls. The canister would preferably provide an appropriate aspect ratio of D: H for a typical pediatric blood loss volume. The D (diameter) of the device would typically be between 2 and 3 inches, and have an H (height) of about 2 inches to about 3 inches. With these smaller dimensions, a collected blood loss volume would provide a reasonably rapid yet monitorable sedimentation rate of RBCS so as to alert an attending physician if an amount of blood loss has reached a volume where transfusion to the pediatric patient is in order. It would be preferred that a sedimentation rate would be achieved that provides for RBC sedimentation within 15 minutes of blood collected in the canister.

Figure 14:
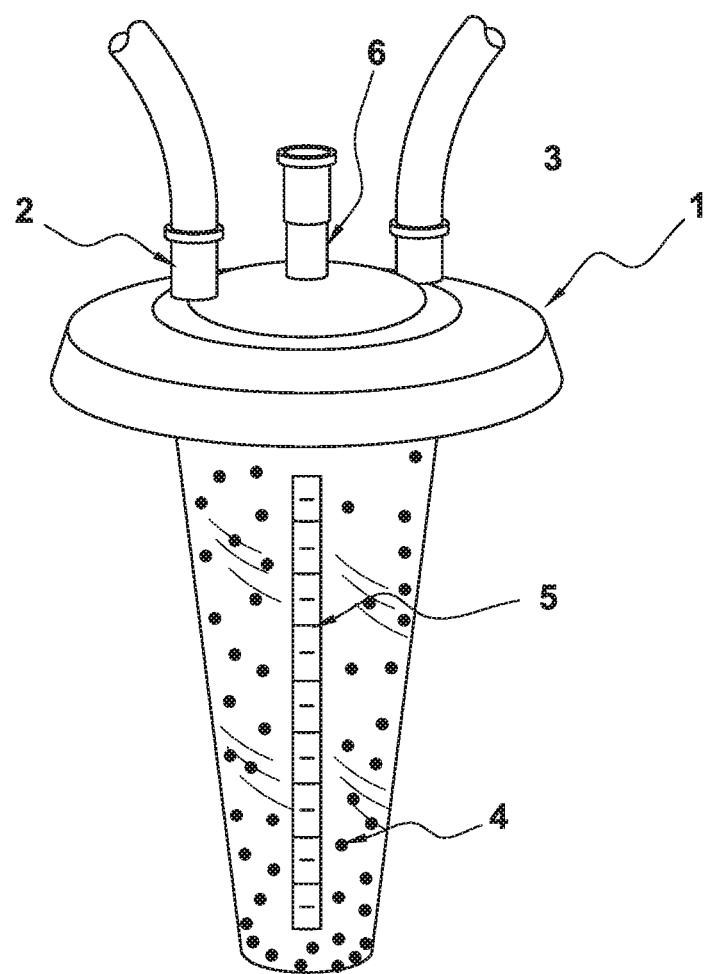
FIG. 14. Conical collection device with flocculant (Critical volume and Pediatric applications), having a BIP (5), RBC flocculant (4), an inlet port (2), a vacuum port (6) and a second inlet port (3).

In some embodiments, the 250 ml container has a conical shape (FIG. 14). The flocculant will be provided to the container either at the time of the surgical intervention event, or may be provided as a pretreatment to the canister (such as by a spray coating).

The amount of flocculant to be added to a 250 ml collection device would be about 50 mg to about 150 mg, or about 125 mg, or an amount sufficient to achieve at least a 0.3%, 0.4% or 0.75% of total volume of the solution.

For sake of description, the following average total blood volume in a pediatric group of patients may be used in calculating when a 12% or greater blood loss has occurred. An average hematocrit value may also be calculated for the class/group (premature neonate, full term neonate, infant) of pediatric patients, and a marking provided alongside one axis of the canister, of average hematocrit values for these patient groups, so as to provide a ready visual reference for the attending physician or anesthesiologist to refer to and compare as against the hematocrit obtained for the patient undergoing the procedure:

Premature Neonates 95 ml/kg
Full Term Neonates 85 ml/kg
Infants 80 ml/kg

The total approximation of blood volume may be calculated by the formula using the average hematocrit of for a human child of a particular weight range and/or age, or for a human adult male or adult female, the $V_m$ (observable settled RBC volume in ml), and the packed ratio value (n) determined for human blood. With multiple human blood sample assessments of settled RBC volume ($V_m$) and Hct information, a visual blood volume indicator panel to be located along the vertical axis of the collection canister may be prepared for the human, and especially for a pediatric human model. This would provide an immediately visually discernable approximation of blood volume in volumes less than about 250 ml, contained in a biological fluid containing human blood. The development of a vertical canister or other receptacle having a Blood Indicator Panel for human blood volume assessment in a liquid, and especially for assessing small volumes of human blood loss, may be developed by one of ordinary skill in the art given the teachings provided herein, without more than a routine and ordinary amount of trial and error.

Example 12

Collapsible Treated Containers for Blood Loss Collection

The present example presents a collapsible plastic-like container (bag) that may be used to collect biological fluid loss, and used to estimate blood loss. Such a collection device is envisioned to be especially useful in combat situations, or any other situation where space for medical equipment is limited.

It is envisioned that the plastic bag containers will include an amount of an RBC flocculant suitable for providing the RBC sedimentation and the blood loss estimate features described herein. In some aspects, the bag could be placed within a supporting container, such as a box, canister, or other structure. The bag may also include a number of markings along the vertical axis of the bag, corresponding to volumetric measures (such as milliliters).

Figure 11A:
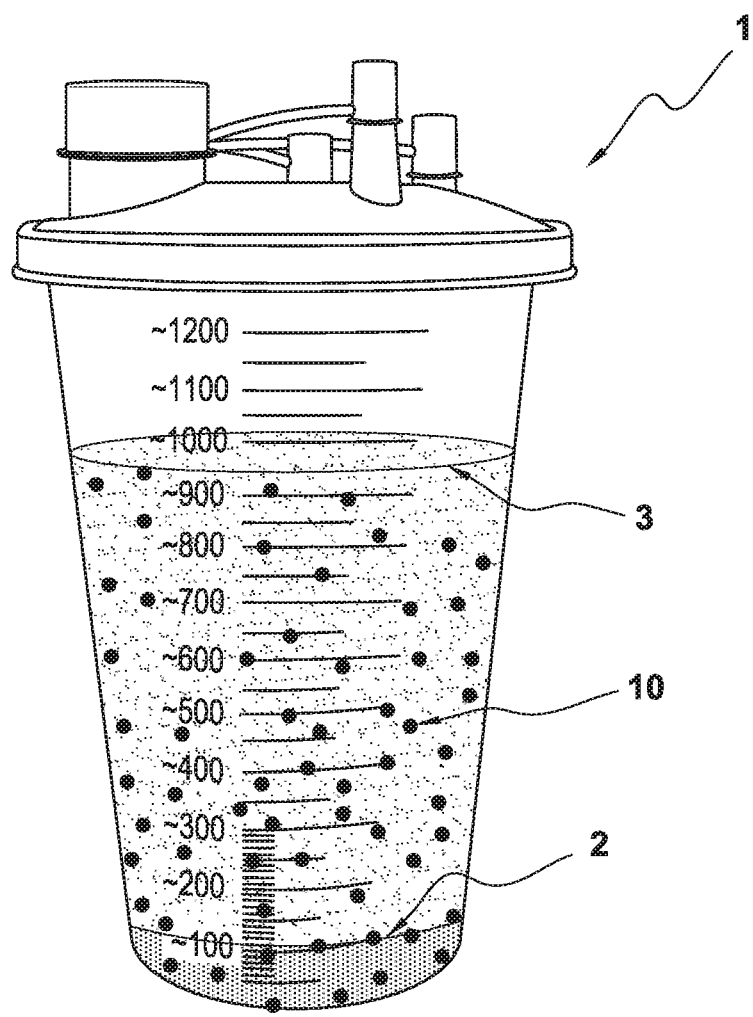
FIG. 11B—A stable settlement of RBCs after about 15-20 minutes in the 40% bovine blood/saline mixture in the polyDADMAC (flocculant particles, 10) coated 1200 ml canister (1). The settled RBC volume in the canister was observed at a volume level of about 240 ml. (2) and a total volume of about 1150 ml. (3), according to the conventional volumetric graduations on the canister.
Figure 11B:
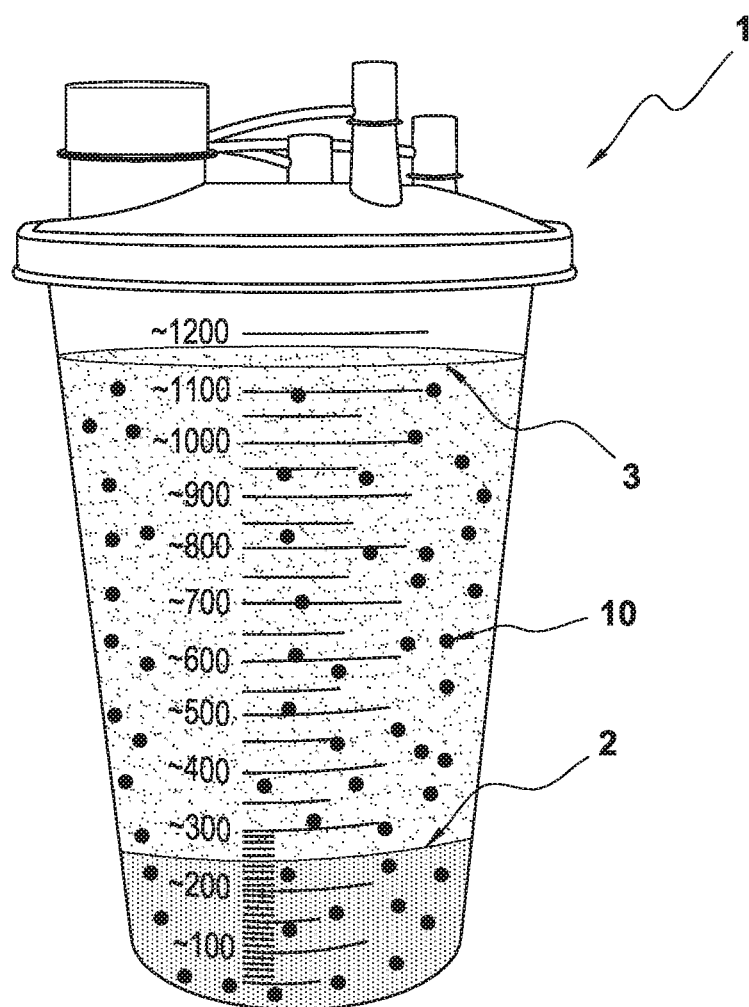
Figure 13:
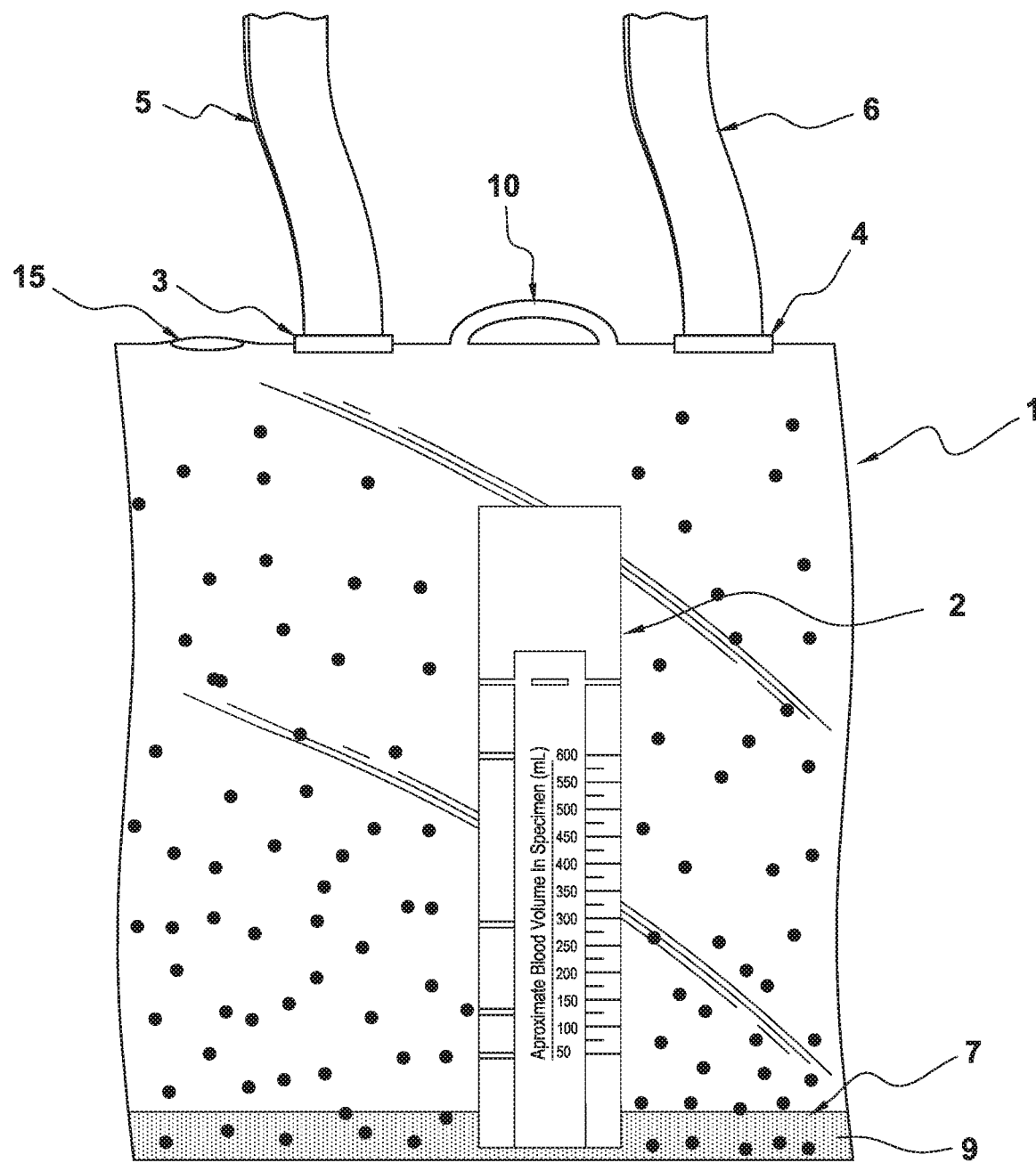
FIG. 13. Collapsible plastic bag blood receptacle with flocculant, having a BIP (20), an inlet port (3), a vacuum port (4) to be placed on the container, and a second inlet port (15) to permit addition of saline or other diluent. The bag should also include a hook (10) fashioned to permit the bag to be placed on an intravenous pole or other mounting.

In some aspects, a clear plastic bag having a volume capacity of about 1,000 ml containing between about 300 milligrams and about 4,700 milligrams of a flocculant, such as polyDADMAC, will be placed in the bag. The bag will include, in some embodiments, calibrated demarcations at a 50 ml, 100 ml, 200 ml, 250 ml, 400 ml, 500 ml, 600 ml, 750 ml and 1 liter marker. The bag may also include a BIP, such as in the form of an adhesive strip, which may be placed on the bag and used to provide a visually discernable indicator of approximated blood volume in a liquid based on the settled RBC level in the collection bag/container. An exemplary rendition of this embodiment is provided at FIG. 13. An insert bag having the RBC flocculant and calibrated BIP for human blood designed for a 1200 ml collection canister, such as the canister shown at FIG. 11A, is also provided. In such embodiments, the canister itself need not be treated with RBC flocculent, and instead, the insert bag will contain the RBC flocculent. The insert bag may also optionally also include a calibrated BIP for human blood.

Example 13

Blood Loss Collection Kit

The flocculant containing canisters (1.2 ml, 500 ml., 250 ml., 10 ml), that includes a blood volume indicator panel, may be provided together as a kit with a length of aspiration tubing and a second length of tubing suitable for adding saline into a canister and/or collapsible envelope.

An instructional insert may be provided as part of the kit for the end user.

Example 14

Stability Testing High Temperature Ageing

This example demonstrates the stability of the RBC flocculant polyDADMAC and retained activity for providing RBC coalescence (flocculation) in a fluid containing blood, after exposure of the polyDADMAC coated canister to high temperatures.

In the present study, the flocculant used was polyDADMAC provided as a coating on a canister for collecting a material, such as a biological liquid material collected during a surgical procedure that will contain a component of blood. The coated canisters were incubated at 55° C. for 6 weeks (equivalent to one-year shelf life at room temperature). The coated canisters, after high temperature aging, were then compared in the function test with the coated canister without going through the high temperature aging test.

Materials:
1) Control Group—four Canisters (Cardinal Health), coated with 600 mg of polyDADMAC (FIG. 1), allowed to dry overnight at room temperature 22° C.).
2) Experimental Group—four Canisters (Cardinal Health), coated with 600 mg of polyDADMAC, allowed to dry overnight at room temperature 22° C.). Then the canisters were incubated in a convection oven set at 55° C. for six weeks.
3) Bovine whole blood (Innovative Research Lot #24301), stored in refrigerator and warm up to room temperature before the experiment.
4) Isotonic Saline (Thermo Scientific, Lot #994448) at room temperature.

Methods:
1) Four canisters were chosen randomly from the experimental and control lots, respectively.
2) Bovine whole blood purchased from a commercial vender (sodium citrate containing), was mixed with isotonic saline at room temperature to the concentrations of 20% and 40% v/v of blood, respectively. The 20% blood mixture had a total volume of 1000 ml and the 40% blood mixture had a total volume of 500 ml.
3) Canisters were tested two at a time: one experimental vs. one control. Mixed blood and saline solutions were introduced into the canister via vacuum aspiration.
4) The settlement of the red blood volume was recorded every minute for 20 minutes, according to the existing graduations on the canister.
5) After 20 minutes, images were taken comparing the two groups.
6) Data was charted as a function of RBC settlement volume vs. time for comparison.

Figure 16A:
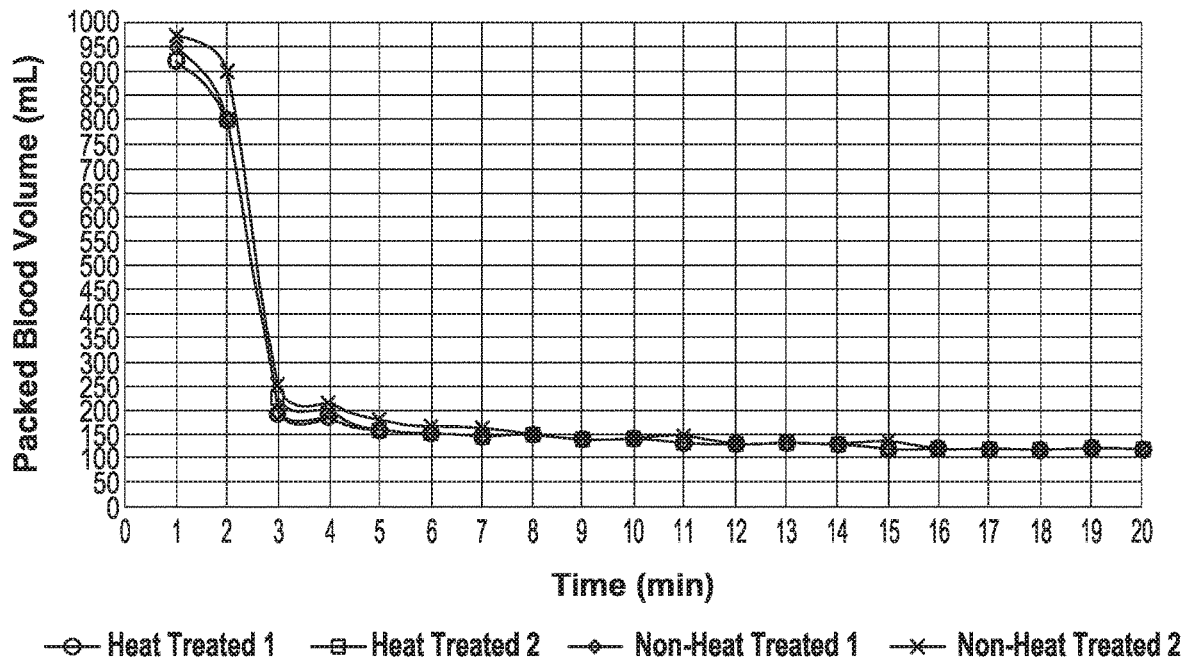
FIG. 16A-16B. Charted data of rate of RBC sedimentation in control (not heat-treated flocculant coated canisters) and experimental (heat-treated flocculant coated) canisters. The tests were performed using 1000 ml of a 20% blood with saline mixture (16A), and 500 ml of a 40% blood with saline mixture (16B). The heat treated canisters maintained the ability to flocculate the RBCs in both of the 20% and the 40% blood/saline mixtures introduced into the canisters within 3 minutes (FIG. 16A) and within 6 minutes (FIG. 16B) of coming in contact with the flocculant containing canister.
Figure 16B:
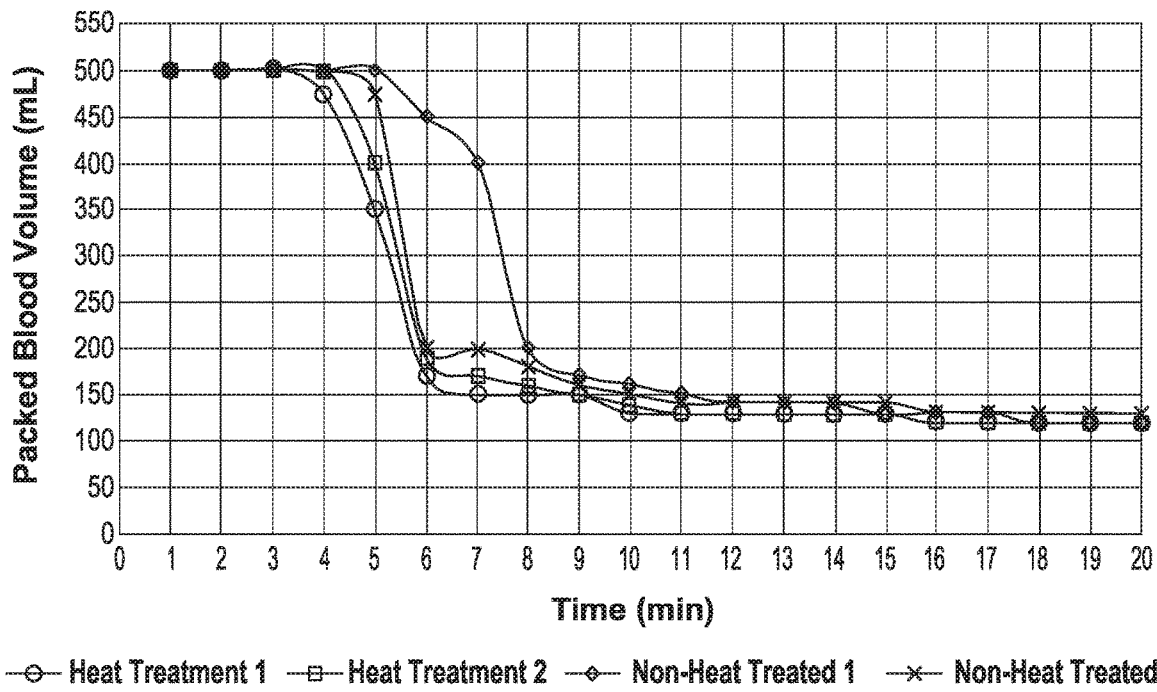
Figure 17A:
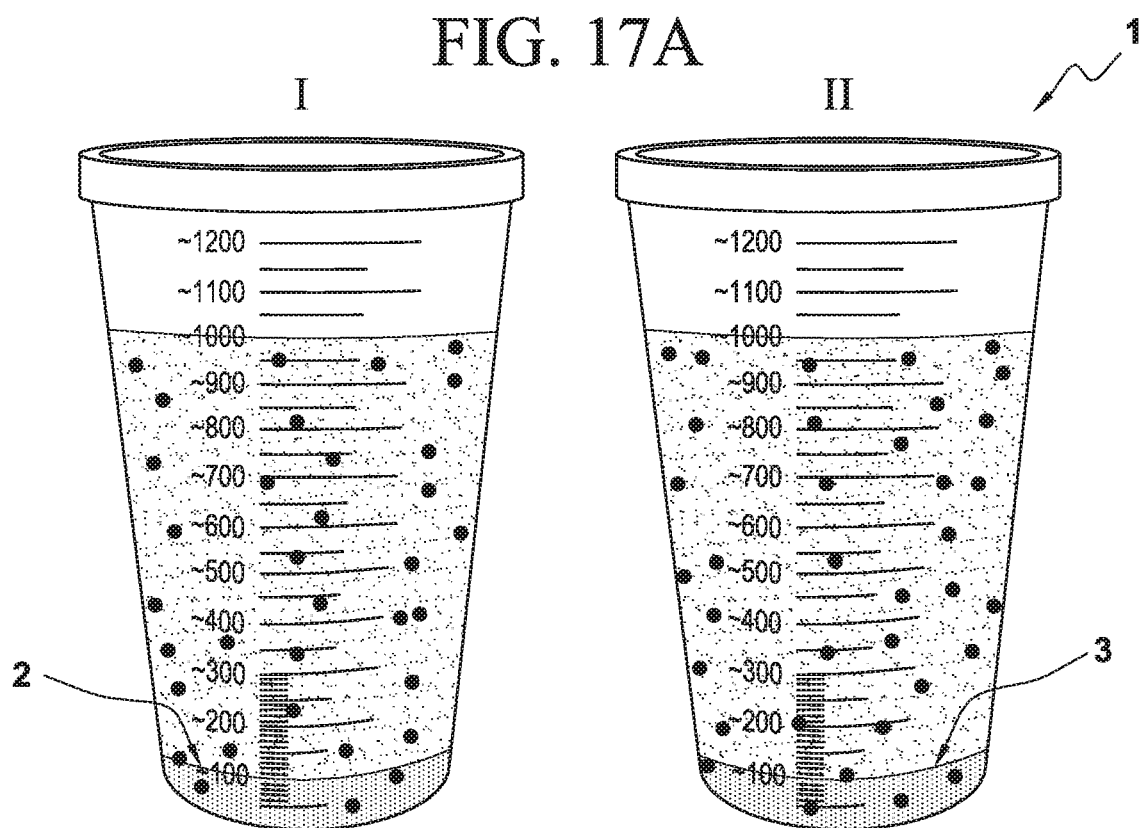
FIG. 17A-FIG. 17B. Settlement of RBCs from bovine blood in a high temperature aged flocculant coated canister (FIG. 17A, Panel I (20% blood), FIG. 17B, Panel I (40% blood) compared to non-high temperature treated flocculant canisters (FIG. 17A, Panel II (20% blood), FIG. 17B, Panel II (40% blood).
Figure 17B:
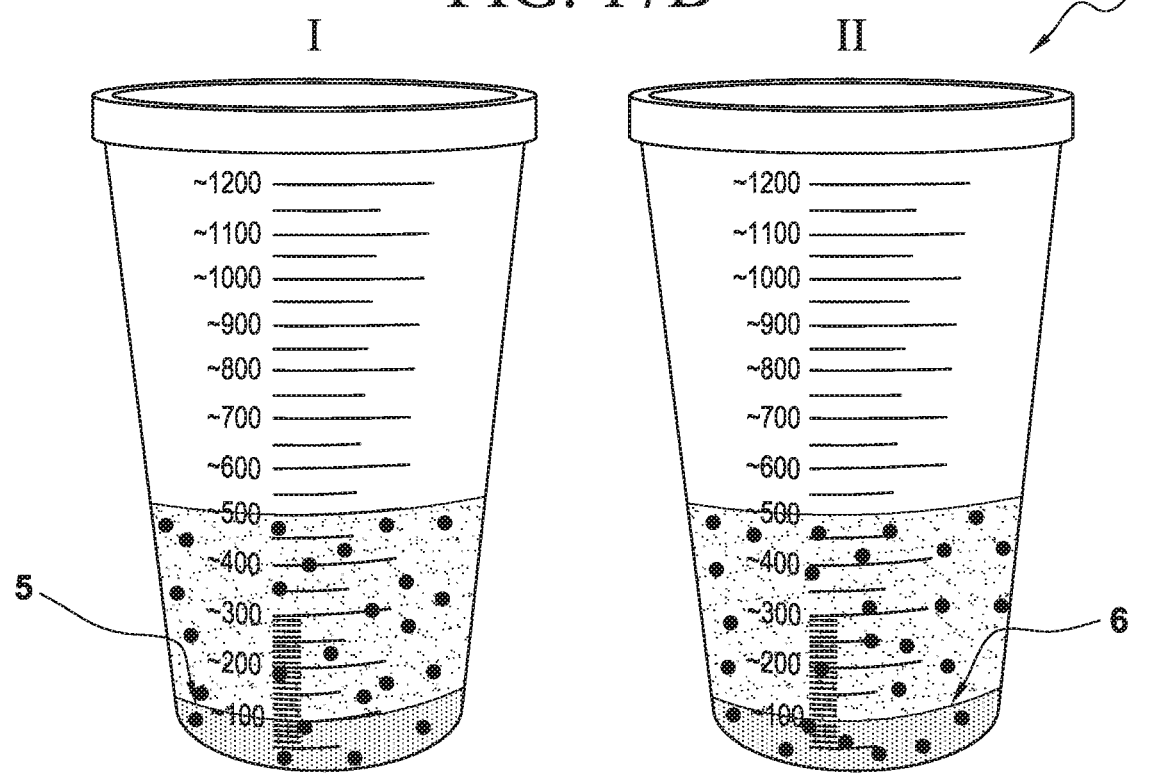

Results: FIGS. 16 A and 16B compares the settlement of RBCs after blood saline mixtures were introduced to the control and experimental (heat-treated) canisters. The tests were performed using 1000 ml of 20% blood with saline mixture (FIG. 16A), and 500 ml of 40% blood with saline mixture (FIG. 16B). Both contain 200 ml of bovine blood. Each test was repeated once. The data illustrates a closely overlay of the volume change curves of RBC settlement in the 20% blood test. All RBC volume settlements were stabilized around 125 ml around 15 minutes after the mixtures were introduced the into the control and experimental canisters. In the 40% blood test, although the volume settlement of one experiment was lagged, all the volume settlements were stabilized around 125 ml after 15 minutes. FIG. 17 illustrates the pictures of the settled RBCs in both control and experimental canisters. FIG. 17A (Panels I and II) and FIG. 17B (Panels I and II) compares the settlement of RBCs after blood and saline mixtures were introduced to the control and experimental (heat-treated) canisters. The tests were performed using 1000 ml of 20% bovine blood with saline mixture (FIG. 17A), and 500 ml of 40% blood with saline mixture (FIG. 17B). Both fluids were known to contain 200 ml of bovine blood. Each test was repeated once.

The data illustrates a closely overlay of the volume change curves of RBC settlement in the 20% blood test. All RBC volume settlement levels were stabilized around 125 ml at about 15 minutes after the mixtures were introduced into the control (FIG. 17A) and experimental (FIG. 17B) canisters.

In the 40% blood test, although the volume settlement of one experiment lagged, the volume of settled RBCs was stabilized at about the 125 ml volumetric mark after 15 minutes. FIGS. 17A and 17B illustrate the settled RBC volumes in the control (17A) and experimental (17B) canisters.

The studies demonstrated no discernable difference in the function between the control and experimental canisters after heat treatment. The polyDADMAC coated canisters, after six-week of aging test under 55° C., show no functional degradation of the polyDADMAC or decrease in effectiveness for facilitating floculation of RBCs in a liquid. The floculent coated cannisters (polyDADMAC coated canisters) are expected to have at least a one-year shelf life without loss of the flocculant activity to provide blood volume estimation in a fluid stored at room temperature.

The examples set forth above are provided to give those of ordinary skill in the art a complete disclosure and description of how to make and use the embodiments of the methods for prediction of the selected modifications that may be made to a biomolecule of interest, and are not intended to limit the scope of what the inventors regard as the scope of the disclosure. Modifications of the above-described modes for carrying out the disclosure can be used by persons of skill in the art, and are intended to be within the scope of the following claims.

It is to be understood that the disclosure is not limited to particular methods or systems, which can, of course, vary. It is also to be understood that the terminology used herein is for the purpose of describing particular embodiments only, and is not intended to be limiting.

A number of embodiments of the disclosure have been described. Nevertheless, it will be understood that various modifications may be made without departing from the spirit and scope of the present disclosure. Accordingly, other embodiments are within the scope of the following claims.

We claim:

1. A collection canister comprising:
   a top, an inside surface, and an outside surface, said inside surface comprising a coating consisting of a red blood cell flocculant; and
   a cap configured to fit over the top of the collection canister, the cap comprising at least two ports, wherein at least one port is suitable for receiving a fluid comprising blood into the collection canister.

2. The collection canister of claim 1 having a volume capacity of about 100 ml, about 250 ml, about 500 ml, about 1,000 ml, about 1,200 ml or about 2,000 ml.

3. The collection canister of claim 1 wherein the red blood cell flocculant is polyDADMAC.

4. The collection canister of claim 3 wherein the polyDADMAC is at a concentration of about 0.3% to about 0.75% in the coating.

5. The collection canister of claim 1 wherein at least one of the ports is a patient port.

6. The collection canister of claim 1 wherein the outside surface comprises a series of flocculated red blood cell sedimentation indicator markings, wherein said flocculated red blood cell sedimentation indicator markings correspond to a volume of sedimented flocculated red blood cells in the collection canister.

7. The collection canister of claim 1 wherein the fluid is a surgical fluid.

8. The collection canister of claim 1 wherein the at least one port is suitable for receiving an aspiration tube, and a second port is suitable for imparting a vacuum suction into said collection canister.

9. The collection canister of claim 1 having a volume capacity of about 1,200 ml.

10. A collection canister comprising:
    a top, an internal surface, and an external surface, the internal surface having a coating consisting of a red blood cell flocculant, the coating being configured to release red blood cell flocculant into the collection canister; and
    a cap configured to fit over the top of the collection canister, the cap comprising a port configured to direct fluid into the collection canister and a port for imparting a suction into the collection canister.

11. The collection canister of claim 10, wherein the collection canister has a volume capacity of at least about 1000 ml.

12. The collection canister of claim 10, wherein the red blood cell flocculant is polyDADMAC.

13. The collection canister of claim 12, wherein the coating of polyDADMAC is at a concentration of about 0.3% to about 0.75%.

14. The collection canister of claim 10, wherein the outside surface of the collection canister comprises a series of flocculated red blood cell sedimentation indicator markings.

15. The collection cannister of claim 1 wherein the coating is configured to release the red blood cell flocculant into the collection canister.

* * * * *

UNITED STATES PATENT AND TRADEMARK OFFICE
CERTIFICATE OF CORRECTION

PATENT NO. : 11,293,913 B2
APPLICATION NO. : 16/257876
DATED : April 5, 2022
INVENTOR(S) : Christopher A. Carew and Jian Ling It is certified that error appears in the above-identified patent and that said Letters Patent is hereby corrected as shown below:

In the Specification

At Column 23, Line 42, please delete the formula and replace it with the formula below:
--$V_b = V_m/(35.4\% \times 1.2) = 2.35 \times V_m$--

At Column 24, Line 28, please delete the formula and replace it with the formula below:
--$V_b = V_m/(Hct \times \eta)$--

Signed and Sealed this
First Day of August, 2023

*Katherine Kelly Vidal*

Katherine Kelly Vidal
*Director of the United States Patent and Trademark Office*